(12) United States Patent
Houghton et al.

(10) Patent No.: US 6,521,423 B1
(45) Date of Patent: Feb. 18, 2003

(54) INTRACELLULAR PRODUCTION OF HEPATITIS C E2 POLYPEPTIDES

(75) Inventors: Michael Houghton, Danville, CA (US); Qui-Lim Choo, El Cerrito, CA (US); Sergio Abrignani, Siena (IT); David Chien, Alamo, CA (US); Mark Selby, San Francisco, CA (US); Edward Glazer, Oakland, CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 09/693,596

(22) Filed: Oct. 19, 2000

Related U.S. Application Data

(63) Continuation of application No. 09/073,406, filed on May 6, 1998, now abandoned.
(60) Provisional application No. 60/045,675, filed on May 6, 1997.

(51) Int. Cl.[7] .............................. C12P 21/00; C12N 7/02; C12N 15/08; C12Q 1/70; G01N 33/52
(52) U.S. Cl. ................... 435/69.1; 435/235.1; 435/239; 435/70; 435/91.42; 435/455; 435/5; 435/7.1; 435/7.2; 435/7.21
(58) Field of Search .............................. 435/5, 7.1, 7.2, 435/7.21, 91.42, 41, 235.1, 239, 69.1, 70.1, 455

(56) References Cited

U.S. PATENT DOCUMENTS 5,942,234 A * 8/1999 Ralston et al. ............ 424/228.1

FOREIGN PATENT DOCUMENTS

| WO | WO 92/08734 | 5/1992 |
| WO | WO 96/04301 | 2/1996 |
| WO | WO 96/04385 | 2/1996 |

OTHER PUBLICATIONS

Coding JW, Monoclonal antibodies: Principles and Practice. Third Edition, Edited by Coding JW, 1996. See section 4.5 on pp. 56 through p. 57.*
Struyf et al. Eur. J. Immunol. 1998, vol. 28, pp. 1262–1271.*
Hsu et al., Clinics in Liver disease 1999, vol. 3, pp. 901–915.*
Inudoh et al., "Antigenicity of Hepatitis C Virus Envelope Proteins Expressed in Chinese Hamster Ovary Cells," *Vaccine* 14 (*17/18*):1590–1596 (1996).
Lanford et al., "Analysis of Hepatitis C Virus Capsid, E1, and E2/NS1 Proteins Expressed in Insect Cells," *Virology* 197:225–235 (1993).
Matsuura et al., "Expression of Processed Envelope Protein of Hepatitis C Virus in Mammalian and Insect Cells," *Journal of Virology* 66(3):1425–1431 (1992).
Matsuura et al., *Virology* 205:141–150 (1994).
Nishihara et al., "Secretion and Purification of Hepatitis C Virus NS1 Glycoprotein Produced by Recombinant Baculovirus–Infected Insect Cells," *Gene* 129:207–214 (1993).
Ralston et al., "Characterization of Hepatitis C Virus Envelope Glycoprotein Complexes Expressed by Recombinant Vaccinia Viruses," *Journal of Virology* 67(*11*):6753–6761 (1993).
Spaete et al., "Characterization of the Hepatitis C Virus E2/NS1 Gene Product Expressed in Mammalian Cells," *Virology* 188:819–830 (1992).

\* cited by examiner

*Primary Examiner*—Ali R. Salimi
*Assistant Examiner*—Bao Qun Li
(74) *Attorney, Agent, or Firm*—Dahna S. Pasternak; Alisa A. Herbin; Robert P. Blackburn

(57) ABSTRACT

Methods for obtaining recombinantly produced, C-terminally truncated, E1 and E2 polypeptides from cell lysates are disclosed. The intracellularly expressed truncated molecules display improved biological properties as compared to their secreted counterparts.

13 Claims, 9 Drawing Sheets

170 METILECYSSERPHESERILEPLIELEULEUALALEULEUSERCYSLEUTHRVALPROALA
ATGATTTGCTCTTTCTCTATCTTCCTTCTGGCCCTGCTCTCTTGCTTGACTGTGCCCGCT
TACTAAACGAGAAAGAGATAGAAGGAAGACCGGGACGAGAGAACGAACTGACACGGGCGA

Mature E1
190 SERALATYRGLNVALARGASNSERTHRGLYLEUTYRHISVALTHRASNASPCYSPROASN
TCGGCCTACCAAGTGCGCAACTCCACGGGGCTCTACCACGTCACCAATGATTGCCCTAAC
AGCCGGATGGTTCACGCGTTGAGGTGCCCCGAGATGGTGCAGTGGTTACTAACGGGATTG 210 SERSERILEVALTYRGLUALAALAASPALAILELEUHISTHRPROGLYCYSVALPROCYS
TCGAGTATTGTGTACGAGGCGGCCGATGCCATCCTGCACACTCCGGGGTGCGTCCCTTGC
AGCTCATAACACATGCTCCGCCGGCTACGGTAGGACGTGTGAGGCCCCACGCAGGGAACG 230 VALARGGLUGLYASNALASERARGCYSTRPVALALAMETTHRPROTHRVALALATHRARG
GTTCGTGAGGGCAACGCCTCGAGGTGTTGGGTGGCGATGACCCCTACGGTGGCCACCAGG
CAAGCACTCCCGTTGCGGAGCTCCACAACCCACCGCTACTGGGGATGCCACCGGTGGTCC 250 ASPGLYLYSLEUPROALATHRGLNLEUARGARGHISILEASPLEULEUVALGLYSERALA
GATGGCAAACTCCCCGCGACGCAGCTTCGACGTCACATCGATCTGCTTGTCGGGAGCGCC
CTACCGTTTGAGGGGCGCTGCGTCGAAGCTGCAGTGTAGCTAGACGAACAGCCCTCGCGG 270 THRLEUCYSSERALALEUTYRVALGLYASPLEUCYSGLYSERVALPHELEUVALGLYGLN
ACCCTCTGTTCGGCCCTCTACGTGGGGGACCTCTGCGGGTCTGTCTTTCTTGTCGGCCAA
TGGGAGACAAGCCGGGAGATGCACCCCCTGGAGACGCCCAGACAGAAAGAACAGCCGGTT 290 LEUPHETHRPHESERPROARGARGHISTRPTHRTHRGLNGLYCYSASNCYSSERILETYR
CTGTTTACCTTCTCTCCCAGGCGCCACTGGACGACGCAAGGTTGCAATTGCTCTATCTAT
GACAAATGGAAGAGAGGGTCCGCGGTGACCTGCTGCGTTCCAACGTTAACGAGATAGATA 310 PROGLYHISILETHRGLYHISARGMETALATRPASPMETMETMETASNTRPSERPROTHR
CCCGGCCATATAACGGGTCACCGCATGGCATGGGATATGATGATGAACTGGTCCCCTACG
GGGCCGGTATATTGCCCAGTGGCGTACCGTACCCTATACTACTACTTGACCAGGGGATGC 330 THRALALEUVALMETALAGLNLEULEUARGILEPROGINALAILELEUASPMETILEALA
ACGGCGTTGGTAATGGCTCAGCTGCTCCGGATCCCACAAGCCATCTTGGACATGATCGCT
TGCCGCAACCATTACCGAGTCGACGAGGCCTAGGGTGTTCGGTAGAACCTGTACTAGCGA C-terminal Anchor
350 GLYALAHISTRPGLYVALLEUALAGLYILEALATYRPHESERMETVALGLYASNTRPALA
GGTGCTCACTGGGGAGTCCTGGCGGGCATAGCGTATTTCTCCATGGTGGGGAACTGGGCG
CCACGAGTGACCCCTCAGGACCGCCCGTATCGCATAAGAGGTACCACCCCTTGACCCGC 370 LYSVALLEUVALVALVALLEULEULEUPHEALAGLYOP
AAGGTCCTGGTAGTGCTGCTGCTATTTGCCGGCTGA
TTCCAGGACCATCACGACGACGATAAACGGCCGACT

FIG. I

```
364  METVALGLYASNTRPALALYSVALLEUVALVALLEULEULEUPHEALAGLYVALASPALA
     ATGGTGGGGAACTGGGCGAAGGTCCTGGTAGTGCTGCTGCTATTTGCCGGCGTCGACGCG
     TACCACCCCTTGACCCGCTTCCAGGACCATCACGACGACGATAAACGGCCGCAGCTGCGC

MATURE E2
384  GLUTHRHISVALTHRGLYGLYSERALAGLYHISTHRVALSERGLYPHEVALSERLEULEU
     GAAACCCACGTCACCGGGGGAAGTGCCGGCCACACTGTGTCTGGATTTGTTAGCCTCCTC
     CTTTGGGTGCAGTGGCCCCCTTCACGGCCGGTGTGACACAGACCTAAACAATCGGAGGAG

404  ALAPROGLYALALYSGINASNVALGINLEULLEASNTHRASNGLYSERTRPHISLEUASN
     GCACCAGGCGCCAAGCAGAACGTCCAGCTGATCAACACCAACGGCAGTTGGCACCTCAAT
     CGTGGTCCGCGGTTCGTCTTGCAGGTCGACTAGTTGTGGTTGCCGTCAACCGTGGAGTTA

424  SERTHRALALEUASNCYSASNASPSERLEUASNTHRGLYTRPLEUALAGLYLEUPHETYR
     AGCACGGCCCTGAACTGCAATGATAGCCTCAACACCGGCTGGTTGGCAGGGCTTTTCTAT
     TCGTGCCGGGACTTGACGTTACTATCGGAGTTGTGGCCGACCAACCGTCCCGAAAAGATA

444  HISHISLYSPHEASNSERSERGLYCYSPROGLUARGLEUALASERCYSARGPROLEUTHR
     CACCACAAGTTCAACTCTTCAGGCTGTCCTGAGAGGCTAGCCAGCTGCCGACCCCTTACC
     GTGGTGTTCAAGTTGAGAAGTCCGACAGGACTCTCCGATCGGTCGACGGCTGGGGAATGG

464  ASPPHEASPGLNGLYTRPGLYPROILESERTYRALAASNGLYSERGLYPROASPGLNARG
     GATTTTGACCAGGGCTGGGGCCCTATCAGTTATGCCAACGGAAGCGGCCCCGACCAGCGC
     CTAAAACTGGTCCCGACCCCGGGATAGTCAATACGGTTGCCTTCGCCGGGGCTGGTCGCG

484  PROTYRCYSTRPHISTYRPROPROLYSPROCYSGLYILEVALPROALALYSSERVALCYS
     CCCTACTGCTGGCACTACCCCCCAAAACCTTGCGGTATTGTGCCCGCGAAGAGTGTGTGT
     GGGATGACGACCGTGATGGGGGGTTTTGGAACGCCATAACACGGGCGCTTCTCACACACA
```

FIG. 2A

504  GLYPROVALTYRCYSPHETHRPROSERPROVALVALVALGLYTHRTHRASPARGSERGLY
     GGTCCGGTATATTGCTTCACTCCCAGCCCCGTGGTGGTGGGAACGACCGACAGGTCGGGC
     CCAGGCCATATAACGAAGTGAGGGTCGGGGCACCACCACCCTTGCTGGCTGTCCAGCCCG

524  ALAPROTHRTYRSERTRPGLYGLUASNASPTHRASPVALPHEVALLEDASNASNTHRARG
     GCGCCCACCTACAGCTGGGGTGAAAATGATACGGACGTCTTCGTCCTTAACAATACCAGG
     CGCGGGTGGATGTCGACCCCACTTTTACTATGCCTGCAGAAGCAGGAATTGTTATGGTCC

544  PROPROLEUGLYASNTRPPHEGLYCYSTHRTRPMETASNSERTHRGLYPHETHRLYSVAL
     CCACCGCTGGGCAATTGGTTCGGTTGTACCTGGATGAACTCAACTGGATTCACCAAAGTG
     GGTGGCGACCCGTTAACCAAGCCAACATGGACCTACTTGAGTTGACCTAAGTGGTTTCAC

564  CYSGLYALAPROPROCYSVALILEGLYGLYALAGLYASNASNTHRLEUHISCYSPROTHR
     TGCGGAGCGCCTCCTTGTGTCATCGGAGGGCGGGCAACAACACCCTGCACTGCCCCACT
     ACGCCTCGCGGAGGAACACAGTAGCCTCCCCGCCCGTTGTTGTGGGACGTGACGGGGTGA

584  ASPCYSPHEARGLYSHISPROASPALATHRTYRSERARGCYSGLYSERGLYPROTRPILE
     GATTGCTTCCGCAAGCATCCGGACGCCACATACTCTCGGTGCGGCTCCGGTCCCTGGATC
     CTAACGAAGGCGTTCGTAGGCCTGCGGTGTATGAGAGCCACGCCGAGGCCAGGGACCTAG

604  THRPROARGCYSLEUVALASPTYRPROTYRARGLEUTRPHISTYRPROCYSTHRILEASN
     ACACCCAGGTGCCTGGTCGACTACCCGTATAGGCTTTGGCATTATCCTTGTACCATCAAC
     TGTGGGTCCACGGACCAGCTGATGGGCATATCCGAAACCGTAATAGGAACATGGTAGTTG

624  TYRTHRILEPHELYSILEARGMETTYRVALGLYGLYVALGLUHISARGLEUGLUALAALA
     TACACCATATTTAAAATCAGGATGTACGTGGGAGGGGTCGAACACAGGCTGGAAGCTGCC
     ATGTGGTATAAAITTTAGTCCTACATGCACCCTCCCCAGCTTGTGTCCGACCTTCGACGG

FIG. 2B

```
644  CYSASNTRPTHRARGGLYGLUARGCYSASPLEUGLUASPARGASPARGSERGLULEUSER
     TGCAACTGGACGCGGGGCGAACGTTGCGATCTGGAAGATAGGGACAGGTCCGAGCTCAGC
     ACGTTGACCTGCGCCCCGCTTGCAACGCTAGACCTTCTATCCCTGTCCAGGCTCGAGTCG

664  PROLEULEULEUTHRTHRTHRGLNTRPGLNVALLEUPROCYSSERPHETHRTHRLEUPRO
     CCGTTACTGCTGACCACTACACAGTGGCAGGTCCTCCCGTGTTCCTTCACAACCCTGCCA
     GGCAATGACGACTGGTGATGTGTCACCGTCCAGGAGGGCACAAGGAAGTGTTGGCACGGT

684  ALALEUSERTHRGLYLEUILEHISLEUHISGLNASNILEVALASPVALGLNTYRLEUTYR
     GCCTTGTCCACCGGCCTCATCCACCTCCACCAGAACATTGTGGACGTGCAGTACTTGTAC
     CGGAACAGGTGGCCGGAGTAGGTGGAGGTGGTCTTGTAACACCTGCACGTCATGAACATG

704  GLYVALGLYSERSERILEALASERTRPALAILELYSTRPGLUTYRVALVAILEULEUPHE
     GGGGTGGGGTCAAGCATCGCGTCCTGGGCCATTAAGTGGGAGTACGTCGTCCTCCTGTTC
     CCCCACCCCAGTTCGTAGCGCAGGACCCGGTAATTCACCCTCATGCAGCAGGAGGACAAG
                      C-terminal Anchor
724  LEULEULEUALAASPALAARGVALCYSSERCYSLEUTRPMETMETLEULEUILESERGLN
     CTTCTGCTTGCAGACGCGCGCGTCTGCTCCTGCTTGTGGATGATGCTACTCATATCCCAA
     GAAGACGAACGTCTGCGCGCGCAGACGAGGACGAACACCTACTACGATGAGTATAGGGTT P7
744  ALAGLUALAALALEUGLUASNLEUVALILELEUASNALAALASERLEUALAGLYTHRHIS
     GCGGAAGCGGCTTTGGAGAACCTCGTAATACTTAATGCAGCATCCCTGGCCGGGACGCAC
     CGCCTTCGCCGAAACCTCTTGGAGCATTATGAATTACGTCGTAGGGACCGGCCCTGCGTG 764  GLYLEUVALSERPHELEUVALPHEPHECYSPHEALATRPTYRLEULYSGLYLYSTRPVAL
     GGTCTTGTATCCTTCCTCGTGTTCTTCTGCTTTGCATGGTATCTGAAGGGTAAGTGGGTG
     CCAGAACATAGGAAGGAGCACAAGAAGACGAAACGTACCATAGACTTCCCATTCACCCAC
```

FIG. 2C

```
784  PROGLYALAVALTYRTHRPHETYRGLYMETTRPPROLEULEULEULEULEULEUALALEU
     CCCGGAGCGGTCTACACCTTCTACGGGATGTGGCCTCTCCTCCTGCTCCTGTTGGCGTTG
     GGGCCTCGCCAGATGTGGAAGATGCCCTACACCGGAGAGGAGGACGAGGACAACCGCAAC

NS2
804  PROGLNARGALATYRALALEUASPTHRGLUVALALALAALASERCYSGLYGLYVALVALLEU
     CCCCAGCGGGCGTACGCGCTGGACACGGAGGTGGCCGCGTCGTGTGGCGGTGTTGTTCTC
     GGGGTCGCCCGCATGCGCGACCTGTGCCTCCACCGGCGCAGCACACCGCCACAACAAGAG

824  VALGLYLEUMETALALEUTHRLEUSERPROTYRTYRLYSARGTYRILESERTRPCYSLEU
     GTCGGGTTGATGGCGCTAACTCTGTCACCATATTACAAGCGCTATATCAGCTGGTGCTTG
     CAGCCCAACTACCGCGATTGAGACAGTGGTATAATGTTCGCGATATAGTCGACCACGAAC

844  TRPTRPLEUGLNTYRPHELEUTHRARGVALGLUALAGLNLEUHISVALTRPILEPROPRO
     TGGTGGCTTCAGTATTTTCTGACCAGAGTGGAAGCGCAACTGCACGTGTGGATTCCCCCC
     ACCACCGAAGTCATAAAAGACTGGTCTCACCTTC-CGTTGACGTGCACACCTAAGGGGGG

864  LEUASNVALARGGLYGLYARGASPALAVALILELEULEUMETCYSALAVALHISPROTHR
     CTCAACGTCCGAGGGGGGCGCGACGCCGTCATCTTACTCATGTGTGCTGTACACCCGACT
     GAGTTGCAGGCTCCCCCCGCGCTGCGGCAGTAGAATGAGTACACACGACATGTGGGCTGA

884  LEUVALPHEASPILETHRLYSLEULEULEUALAVALPHEGLYPROLEUTRPILELEUGLN
     CTGGTATTTGACATCACCAAATTGCTGCTGGCCGTCTTCGGACCCCTTTGGATTCTTCAA
     GACCATAAACTGTAGTGGTTTAACGACGACCGGCAGAAGCCTGGGGAAACCTAAGAAGTT

904  ALASERLEULEULYSVALPROTYRPHEVALARGVALGLNGLYLEULEUARGPHECYSALA
     CCCAGTTTGCTTAAAGTACCCTACTTTGTGCGCGTCCAAGGCCTTCTCCGGTTCTGCGCG
     CGGTCAAACGAATTTCATGGGATGAAACACGCGCAGGTTCCGGAAGAGGCCAAGACGCGC
```

FIG. 2D

```
 924   LEUALAARGLYSMETILEGLYGLYHISTYRVALGLNMETVALILEILELYSLEUGLYALA
       TTAGCGCGGAAGATGATCGGAGGCCATTACGTGCAAATGGTCATCATTAAGTTAGGGGCG
       AATCGCGCCTTCTACTAGCCTCCGGTAATGCACGTTTACCAGTAGTAATTCAATCCCCGC

944   LEUTHRGLYTHRTYRVALTYRASNHISLEUTHRPROLEUARGASPTRPALAHISASNGLY
       CTTACTGGCACCTATGTTTATAACCATCTCACTCCTCTTCGGGACTGGGCGCACAACGGC
       GAATGACCGTGGATACAAATATTGGTAGAGTGAGGAGAAGCCCTGACCCGCGTGTTGCCG

964   LEUARGASPLEUALAVALALAVALGLUPROVALVALPHESERGLNMETGLUTHRLYSLEU
       TTGCGAGATCTGGCCGTGGCTGTAGAGCCAGTCGTCTTCTCCCAAATGGAGACCAAGCTC
       AACGCTCTAGACCGGCACCGACATCTCGGTCAGCAGAAGAGGGTTTACCTCTGGTTCGAG

984   ILETHRTRPGLYALAASPTHRALAALACYSGLYASPILEILEASNGLYLEUPROVALSER
       ATCACGTGGGGGGCAGATACCGCCGCGTGCGGTGACATCATCAACGGCTTGCCTGTTTCC
       TAGTGCACCCCCCGTCTATGGCGGCGCACGCCACTGTAGTAGTTGCCGAACGGACAAAGG

1004   ALAARGARGGLYARGGLUILELELEULEUGLYPROALAASPGLYMETVALSERLYSGLYTRP
       GCCCGCAGGGGCCGGGAGATACTGCTCGGGCCAGCCGATGGAATGGTCTCCAAGGGTTGG
       CGGGCGTCCCCGGCCCTCTATGACGAGCCCGGTCGGCTACCTTACCAGAGGTTCCCAACC

1024   ARGLEULEU
       AGGTTGCTG
       TCCAACGAC
```

FIG. 2E

INTRACELLULAR PRODUCTION OF HEPATITIS C E2 POLYPEPTIDES

CROSS-REFERENCE TO RELATED APPLICATIONS

This application is a continuation of U.S. patent application Ser. No. 09/073,406, filed May 6, 1998, now abandoned from which application priority is claimed pursuant to 35 U.S.C. §120, and this application is related to Provisional Patent Application Ser. No. 60/045,675, filed May 6, 1997, from which priority is claimed under 35 USC §119(e)(1), and which applications are incorporated herein by reference in their entireties.

BACKGROUND OF THE INVENTION

1. Technical Field

The present invention pertains generally to viral proteins. In particular, the invention relates to improved methods for isolating truncated forms of hepatitis C virus E1 and E2 proteins having improved biological properties for use in vaccine compositions and as diagnostic reagents.

2. Background of the Invention

Hepatitis C Virus (HCV) is the principal cause of parenteral non-A, non-B hepatitis which is transmitted largely through blood transfusion and sexual contact. The virus is present in 0.4 to 2.0% of blood donors. Chronic hepatitis develops in about 50% of infections and of these, approximately 20% of infected individuals develop liver cirrhosis which sometimes leads to hepatocellular carcinoma. Accordingly, the study and control of the disease is of medical importance.

The viral genomic sequence of HCV is known, as are methods for obtaining the sequence. See, e.g., International Publication Nos. WO 89/04669; WO 90/11089; and WO 90/14436. HCV has a 9.5 kb positive-sense, single-stranded RNA genome and is a member of the Flaviridae family of viruses. At least six distinct, but related genotypes of HCV, based on phylogenetic analyses, have been identified (Simmonds et al., *J. Gen. Virol.* (1993) 74:2391–2399). The virus encodes a single polyprotein having more than 3000 amino acid residues (Choo et al., *Science* (1989) 244:359–362; Choo et al., *Proc. Natl. Acad. Sci. USA* (1991) 88:2451–2455; Han et al., *Proc. Natl. Acad. Sci. USA* (1991) 88:1711–1715). The polyprotein is processed co- and post-translationally into both structural and non-structural (NS) proteins.

In particular, there are three putative structural proteins, consisting of the N-terminal nucleocapsid protein (termed "core") and two envelope glycoproteins, "E1" (also known as E) and "E2" (also known as E2/NS1). (See, Houghton et al., *Hepatology* (1991) 14:381–388, for a discussion of HCV proteins, including E1 and E2.) E1 is detected as a 32–35 kDa species and is converted into a single endo H-sensitive band of approximately 18 kDa. By contrast, E2 displays a complex pattern upon immunoprecipitation consistent with the generation of multiple species (Grakoui et al., *J. Virol.* (1993) 67:1385–1395; Tomei et al., *J. Virol.* (1993) 67:4017–4026.). The HCV E1 and E2 glycoproteins are of considerable interest because they have been shown to be protective in primate studies. (Choo et al., *Proc. Natl. Acad. Sci. USA* (1994) 91:1294–1298).

Full-length E1 and E2 are retained within cells and have been shown to lack complex carbohydrate when expressed stably or in a transient Vaccinia virus system (Spaete et al., *Virology* (1992) 188:819–830; Ralston et al., *J. Virol.* (1993) 67:6753–6761). Since the E1 and E2 proteins are normally membrane-bound in these expression systems, experimenters had previously thought it desirable to produce secreted forms to facilitate purification of the proteins for further use.

For example, an HCV E2 molecule, truncated at amino acid 661 and which is secreted from mammalian cells, has been described. Spaete et al., *Virology* (1992) 188:819–830. The production of truncated, secreted HCV E1 and E2 molecules has also been disclosed in International Publication No. WO 96/04301, published Feb. 15, 1996. Inudoh et al., *Vaccine* (1996) 14:1590–1596, describes the production of an HCV E2 molecule lacking the C-terminal hydrophobic domain. This protein was secreted into culture medium and found to be more antigenic than intracellularly produced counterparts.

Depending on the expression system used, such secreted proteins may not retain the native conformation and may include modified glycosylation patterns. Thus, purification of intracellularly produced HCV E1 and E2 proteins has been attempted in order to preserve the native conformation of the proteins. See, e.g., International Publication No. WO 92/08734, published May 29, 1992.

Despite the above attempts at obtaining HCV E1 and E2, a need still exists for alternative methods of efficiently purifying immunogenic HCV E1 and E2 molecules for use in vaccine compositions and as diagnostic reagents.

SUMMARY OF THE INVENTION

The present invention is based on the isolation of HCV E1 and E2 proteins which display improved biological properties. The proteins are truncated and can be produced using recombinant techniques. Such truncated proteins are normally secreted into culture medium. However, the proteins for use herein are isolated from the cells rather than from culture medium. The molecules so isolated display enhanced receptor-binding abilities, perform better in assays designed to measure the ability of proteins to elicit the production of HCV neutralizing antibodies, and are more immunoreactive and therefore provide improved diagnostic reagents, as compared to their secreted counterparts.

Accordingly, in one embodiment, the subject invention is directed to a method for isolating an HCV E1 polypeptide that lacks a portion of its C-terminus beginning at about amino acid 370, numbered with reference to the HCV1 E1 amino acid sequence. The method comprises:

(a) providing a population of host cells transformed with a polynucleotide comprising a coding sequence for the HCV E1 polypeptide, wherein the coding sequence is operably linked to control elements such that the coding sequence can be transcribed and translated in the host cell;

(b) culturing the population of cells under conditions whereby the HCV E1 polypeptide is expressed intracellularly;

(c) disrupting the host cells; and (d) isolating the HCV E1 polypeptide from the disrupted cells.

In particularly preferred embodiments, the HCV E1 polypeptide produced by the method lacks a portion of its C-terminus beginning at about amino acid 360, numbered with reference to the HCV1 E1 amino acid sequence.

In another embodiment, the invention is directed to a method for isolating an HCV E2 polypeptide that lacks a portion of its C-terminus beginning at about amino acid 730 but not extending beyond about amino acid 625, numbered with reference to the HCV1 E2 amino acid sequence. The method comprises:

(a) providing a population of host cells transformed with a polynucleotide comprising a coding sequence for the HCV E2 polypeptide, wherein the coding sequence is operably linked to control elements such that the coding sequence can be transcribed and translated in the host cell;

(b) culturing the population of cells under conditions whereby the HCV E2 polypeptide is expressed intracellularly;

(c) disrupting the host cells; and (d) isolating the HCV E2 polypeptide from the disrupted cells.

In particularly preferred embodiments, the HCV E2 polypeptide produced by the method lacks at least a portion of its C-terminus beginning at about amino acid 725, numbered with reference to the HCV1 E2 amino acid sequence, and more particularly, lacks a portion of its C-terminus beginning at about amino acid 715, 661 or 655.

Further embodiments of the subject invention pertain to HCV E1 and HCV E2 polypeptides produced by the above methods, as well as vaccine compositions comprising the HCV polypeptides and methods of preparing the vaccine compositions.

In yet other embodiments, the invention is directed to methods of detecting the presence or absence of HCV infection in a subject suspected of having an HCV infection. The methods comprise:

(a) providing a biological sample from the subject;

(b) providing an HCV E1 polypeptide or an HCV E2 polypeptide, as described above; and (c) contacting the biological sample with the CV polypeptide, under conditions which allow HCV antibodies, if present in the biological sample, to bind with the HCV polypeptide, thereby detecting the presence or absence of HCV infection in the subject.

In other embodiments, the invention is directed to immunodiagnostic test kits for detecting HCV infection. The test kits include an HCV E1 or HCV E2 polypeptide, as described above, and instructions for conducting the immunodiagnostic test.

These and other embodiments of the present invention will readily occur to those of ordinary skill in the art in view of the disclosure herein.

BRIEF DESCRIPTION OF THE FIGURES

FIG. 1 shows the full-length nucleotide sequence and corresponding amino acid sequence for HCV1 E1 which includes the N-terminal signal sequence and the C-terminal membrane anchor domain. The nucleic acid sequence given in FIG. 1 is presented as SEQ ID NO:1 and the corresponding amino acid sequence is presented as SEQ ID NO:2.

FIGS. 2A–2E show the full-length nucleotide sequence and the corresponding amino acid sequence for the HCV1 E2/NS2 region which includes the N-terminal signal sequence for E2 and the C-terminal membrane anchor domain for E2. The nucleic acid sequence given in FIGS. 2A–2E is presented as SEQ ID NO:3 and the corresponding amino acid sequence is presented as SEQ ID NO:4.

DETAILED DESCRIPTION OF THE INVENTION

Figure 3:
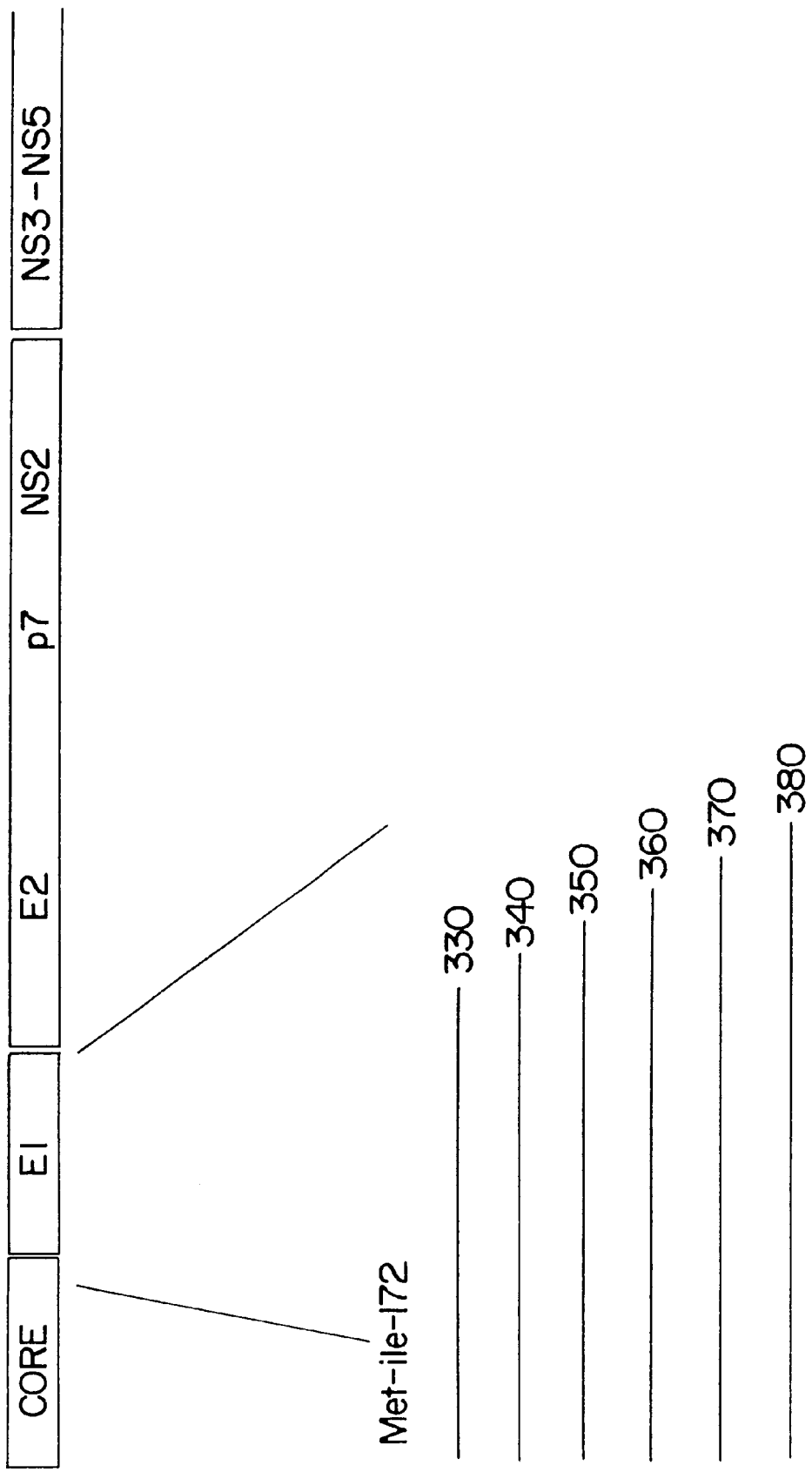
FIG. 3 depicts the HCV E1 cDNA templates described in the Examples. The core through NS2 region is shown on the top and is drawn to scale; the distal NS3 through NS5 is not drawn to scale. The E1 region has been expanded to better display the various templates. The numbers to the right refer to the amino acid endpoint used in each template.

The practice of the present invention will employ, unless otherwise indicated, conventional methods of virology, microbiology, molecular biology and recombinant DNA techniques within the skill of the art. Such techniques are explained fully in the literature. See, e.g., Sambrook, et al. *Molecular Cloning: A Laboratory Manual* (2nd Edition, 1989); *DNA Cloning: A Practical Approach*, vol. I & II (D. Glover, ed.); *Animal Cell Culture* (R. Freshney, ed., 1986); Perbal, *A Practical Guide to Molecular Cloning* (1984); *Fundamental Virology*, 2nd Edition, vol. I & II (B. N. Fields and D. M. Knipe, eds.); *Protein Purification Applications: A Practical Approach*, (E. L. V. Harris and S. Angal, Eds., 1990); and T. E. Creighton, *Proteins: Structures and Molecular Properties* (W. H. Freeman and Company, 1993).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

I. Definitions

In describing the present invention, the following terms will be employed, and are intended to be defined as indicated below.

By an "E1 polypeptide" is meant a molecule derived from an HCV E1 region. The mature E1 region of HCV1 begins at approximately amino acid 192 of the polyprotein and continues to approximately amino acid 383 (see FIG. 1 SEQ ID NO:1 and SEQ ID NO:2). Amino acids at around 173 through approximately 191 serve as a signal sequence for E1. Thus, by an "E1 polypeptide" is meant either a precursor E1 protein, including the signal sequence, or a mature E1 polypeptide which lacks this sequence, or even an E1 polypeptide with a heterologous signal sequence. The E1 polypeptide includes a C-terminal membrane anchor sequence which occurs at approximately amino acid positions 360–383 (see, International Publication No. WO 96/04301, published Feb. 15, 1996).

By an "E2 polypeptide" is meant a molecule derived from an HCV E2 region. The mature E2 region of HCV1 begins at approximately amino acid 383–385 (see FIG. 2 SEQ ID NO:3 and SEQ ID NO:4). A signal peptide begins at approximately amino acid 364 of the polyprotein. Thus, by an "E2 polypeptide" is meant either a precursor E2 protein, including the signal sequence, or a mature E2 polypeptide which lacks this sequence, or even an E2 polypeptide with a heterologous signal sequence. The E2 polypeptide includes a C-terminal membrane anchor sequence which occurs at approximately amino acid positions 715–730 and may extend as far as approximately amino acid residue 746 (see, Lin et al., *J. Virol.* (1994) 68:5063–5073).

Representative E1 and E2 regions from HCV1 are shown in FIGS. 1 and 2, respectively. For purposes of the present invention, the E1 and E2 regions are defined with respect to the amino acid number of the polyprotein encoded by the genome of HCV1, with the initiator methionine being designated position 1. However, it should be noted that the term an "E1 polypeptide" or an "E2 polypeptide" as used herein is not limited to the HCV1 sequence. In this regard, the corresponding E1 or E2 regions in another HCV isolate can be readily determined by aligning sequences from the two isolates in a manner that brings the sequences into maximum alignment. This can be performed with any of a number of computer software packages, such as ALIGN 1.0, available from the University of Virginia, Department of Biochemistry (Attn: Dr. William R. Pearson). See, Pearson et al., *Proc. Natl. Acad. Sci. USA* (1988) 85:2444–2448.

Furthermore, an "E1 polypeptide" or an "E2 polypeptide" as defined herein is not limited to a polypeptide having the exact sequence depicted in the Figures. Indeed, the HCV genome is in a state of constant flux and contains several variable domains which exhibit relatively high degrees of variability between isolates. It is readily apparent that the terms encompass E1 and E2 polypeptides from any of the various HCV isolates including isolates having any of the 6 genotypes of HCV described in Simmonds et al., *J. Gen. Virol.* (1993) 74:2391–2399), as well as newly identified isolates, and subtypes of these isolates, such as HCV1a, HCV1b etc.

Additionally, the terms "E1 polypeptide" and "E2 polypeptide" encompass proteins which include additional modifications to the native sequence, such as additional internal deletions, additions and substitutions (generally conservative in nature). These modifications may be deliberate, as through site-directed mutagenesis, or may be accidental, such as through naturally occurring mutational events. All of these modifications are encompassed in the present invention so long as the modified E1 and E2 polypeptides function for their intended purpose. Thus, for example, if the E1 and/or E2 polypeptides are to be used in vaccine compositions, the modifications must be such that immunological activity (i.e., the ability to elicit an antibody response to the polypeptide) is not lost. Similarly, if the polypeptides are to be used for diagnostic purposes, such capability must be retained.

An E1 or E2 polypeptide "lacking all or a portion of its membrane spanning domain" is an E1 or E2 polypeptide, respectively, as defined above, which has been manipulated to delete all or a part of the membrane anchor sequence which functions to associate the polypeptide to the endoplasmic reticulum. Normally, such a polypeptide is capable of secretion into growth medium in which an organism expressing the protein is cultured. However, for purposes of the present invention, such polypeptides may also be recovered intracellularly. Secretion into growth media is readily determined using a number of detection techniques, including, e.g., polyacrylamide gel electrophoresis and the like, and immunological techniques such as immunoprecipitation assays as described in, e.g., International Publication No. WO 96/04301, published Feb. 15, 1996. With E1, generally polypeptides terminating with about amino acid position 370 and higher (based on the numbering of HCV1 E1) will be retained by the ER and hence not secreted into growth media. With E2, polypeptides terminating with about amino acid position 731 and higher (also based on the numbering of the HCV1 E2 sequence) will be retained by the ER and not secreted. (See, e.g., International Publication No. WO 96/04301, published Feb. 15, 1996). It should be noted that these amino acid positions are not absolute and may vary to some degree.

Although not all possible C-terminal truncations have been exemplified herein, it is to be understood that intervening truncations, such as e.g., E1 polypeptides ending in amino acids 351, 352, 353 and so on, or E2 polypeptides ending in for example amino acids 716, 717, 718 and so on, are also encompassed by the present invention. Hence, all E1 polypeptides, terminating at about amino acids 369 and lower, and all E2 polypeptides, terminating at about amino acids 730 and lower, are intended to be captured by the present invention.

Furthermore, the C-terminal truncation can extend beyond the transmembrane spanning domain towards the N-terminus. Thus, for example, E1 truncations occurring at positions lower than, e.g., 360 and E2 truncations occurring at positions lower than, e.g., 715, are also encompassed by the present invention. All that is necessary is that the truncated E1 and E2 polypeptides remain functional for their intended purpose. However, particularly preferred E1 constructs are those that do not extend beyond about amino acid 300. Preferred E2 constructs are those with C-terminal truncations that do not extend beyond about amino acid position 500. Particularly preferred E2 truncations are those molecules truncated after about amino acid 715, 661 or 655.

An E1 and/or E2 polypeptide is produced "intracellularly" when it is found within the cell, either associated with components of the cell, such as in association with the endoplasmic reticulum (ER) or the Golgi Apparatus, or when it is present in the soluble cellular fraction. The E1 and/or E2 polypeptides of the present invention may also be secreted into growth medium so long as sufficient amounts of the polypeptides remain present within the cell such that they can be purified from cell lysates using techniques described herein.

An "immunogenic" HCV E1 or E2 protein is a molecule that includes at least one epitope such that the molecule is capable of either eliciting an immunological reaction in an individual to which the protein is administered or, in the diagnostic context, is capable of reacting with antibodies directed against the HCV in question.

By "epitope" is meant a site on an antigen to which specific B cells and/or T cells respond, rendering the molecule including such an epitope capable of eliciting an immunological reaction or capable of reacting with HCV antibodies present in a biological sample. The term is also used interchangeably with "antigenic determinant" or "antigenic determinant site." An epitope can comprise 3 or more amino acids in a spatial conformation unique to the epitope. Generally, an epitope consists of at least 5 such amino acids and, more usually, consists of at least 8–10 such amino acids. Methods of determining spatial conformation of amino acids are known in the art and include, for example, x-ray crystallography and 2-dimensional nuclear magnetic resonance. Furthermore, the identification of epitopes in a given protein is readily accomplished using techniques well known in the art, such as by the use of hydrophobicity studies and by site-directed serology. See, also, Geysen et al., *Proc. Natl. Acad. Sci. USA* (1984) 81:3998–4002 (general method of rapidly synthesizing peptides to determine the location of immunogenic epitopes in a given antigen); U.S. Pat. No. 4,708,871 (procedures for identifying and chemically synthesizing epitopes of antigens); and Geysen et al., *Molecular Immunology* (1986) 23:709–715 (technique for identifying peptides with high affinity for a given antibody). Antibodies that recognize the same epitope can be identified in a simple immunoassay showing the ability of one antibody to block the binding of another antibody to a target antigen.

An "immunological response" as used herein is the development in the subject of a humoral and/or a cellular immune response to the E1 and/or E2 polypeptide when the polypeptide is present in a vaccine composition.

These antibodies may also neutralize infectivity, and/or mediate antibody-complement or antibody dependent cell cytotoxicity to provide protection to an immunized host. Immunological reactivity may be determined in standard immunoassays, such as a competition assays, well known in the art.

Two polynucleotides or protein molecules are "substantially homologous" when at least about 40–50%, preferably at least about 70–80%, and most preferably at least about 85–95%, of the nucleotides or amino acids from the molecules match over a defined length of the molecule. As used herein, substantially homologous also refers to molecules having sequences which show identity to the specified nucleic acid or protein molecule. Nucleic acid molecules that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, vols I & II, supra; *Nucleic Acid Hybridization*, supra. For example, homology can be determined by hybridization of polynucleotides under conditions which form stable duplexes between homologous regions. Stable duplexes are those, for example, which withstand digestion with a single-stranded specific nuclease(s), such as S1. Such duplexes can be analyzed by various methods, such as size determination of digested fragments.

"Stringency" refers to conditions in a hybridization reaction that favor association of very similar sequences over sequences that differ. For example, the combination of temperature and salt concentration should be chosen that is approximately 12 to 20 degrees C. below the calculated Tm of the hybrid under study.

Other techniques for determining sequence identity are well known in the art and include determining the sequence of the polynucleotide or polypeptide of interest and comparing this to a second sequence. Programs available in the Wisconsin Sequence Analysis Package, Version 8 (available from Genetics Computer Group, Madison, Wis.) for example, the BESTFIT, FASTA and GAP programs, are capable of calculating identity between two molecules.

An "isolated" or "purified" protein or polypeptide is a protein which is separate and discrete from a whole organism with which the protein is normally associated in nature. It is apparent that the term denotes proteins of various levels of purity. Typically, a composition containing a purified protein will be one in which at least about 35%, preferably at least about 40–50%, more preferably, at least about 75–85%, and most preferably at least about 90% or more, of the total protein in the composition will be the protein in question.

A "coding sequence" or a sequence which "encodes" a selected protein, is a nucleic acid sequence which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to cDNA from viral nucleotide sequences as well as synthetic and semisynthetic DNA sequences and sequences including base analogs. A transcription termination sequence may be located 3' to the coding sequence.

"Control elements" refers collectively to promoter sequences, ribosome binding sites, polyadenylation signals, transcription termination sequences, upstream regulatory domains, enhancers, and the like, which collectively provide for the transcription and translation of a coding sequence in a host cell. Not all of these control elements need always be present so long as the desired gene is capable of being transcribed and translated.

A control element "directs the transcription" of a coding sequence in a cell when RNA polymerase will bind the promoter sequence and transcribe the coding sequence into mRNA, which is then translated into the polypeptide encoded by the coding sequence.

"Operably linked" refers to an arrangement of elements wherein the components so described are configured so as to perform their usual function. Thus, control elements operably linked to a coding sequence are capable of effecting the expression of the coding sequence when RNA polymerase is present. The control elements need not be contiguous with the coding sequence, so long as they function to direct the expression thereof. Thus, for example, intervening untranslated yet transcribed sequences can be present between, e.g., a promoter sequence and the coding sequence and the promoter sequence can still be considered "operably linked" to the coding sequence.

"Recombinant" as used herein to describe a nucleic acid molecule means a polynucleotide of genomic, cDNA, semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide. "Recombinant host cells," "host cells," "cells," "cell lines," "cell cultures," and other such terms denoting procaryotic microorganisms or eucaryotic cell lines cultured as unicellular entities, are used interchangeably, and refer to cells which can be, or have been, used as recipients for recombinant vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

By "vertebrate subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered.

As used herein, a "biological sample" refers to a sample of tissue or fluid isolated from an individual, including but not limited to, for example, blood, plasma, serum, fecal matter, urine, bone marrow, bile, spinal fluid, lymph fluid, samples of the skin, external secretions of the skin, respiratory, intestinal, and genitourinary tracts, samples derived from the gastric epithelium and gastric mucosa, tears, saliva, milk, blood cells, organs, biopsies and also samples of in vitro cell culture constituents including but not limited to conditioned media resulting from the growth of cells and tissues in culture medium, e.g., recombinant cells, and cell components.

The terms "label" and "detectable label" refer to a molecule capable of detection, including, but not limited to, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like. The term "fluorescer" refers to a substance or a portion thereof which is capable of exhibiting fluorescence in the detectable range. Particular examples of labels which may be used with the invention include, but are not limited to fluorescein, rhodamine, dansyl, umbelliferone, Texas red, luminol, acradimum esters, NADPH, α-β-galactosidase, horseradish peroxidase, glucose oxidase, alkaline phosphatase and urease.

II. Modes of Carrying Out the Invention

The present invention is based on the discovery of novel methods for obtaining recombinantly produced, C-terminally truncated, E1 and E2 polypeptides from cell lysates, rather than directly from growth media. As demonstrated herein, the molecules purified in this manner have surprisingly better biological properties than their secreted counterparts. For example, the intracellularly produced molecules display enhanced receptor-binding abilities, exhibit superior performance in assays designed to measure the ability of proteins to elicit the production of HCV neutralizing antibodies, and are more immunoreactive and therefore provide improved diagnostic reagents, as compared to their secreted counterparts.

While not wishing to be bound by any particular theory, the intracellularly expressed forms of HCV E1 and E2 may more closely resemble the native viral proteins due to the carbohydrate motifs present on the molecules, while the secreted glycoproteins may contain modified carbohydrate moieties or glycosylation patterns. Furthermore, the intracellularly produced forms of E1 and E2 may be conformationally different than the secreted forms.

In particular, a number of C-terminally truncated E1 and E2 polypeptides, lacking portions of the membrane spanning domain, have been constructed. See FIGS. 3 and 4, respectively, and the examples. As shown in the examples, a truncated construct terminating at amino acid 715 and termed "$E2_{715}$" herein, is surprisingly more immunoreactive when purified from recombinant cells, than $E2_{715}$ secreted into, and purified from, media. Furthermore, molecules terminating at amino acids 661 and 655 also show enhanced immunoreactivity. Thus, the intracellularly produced truncated HCV polypeptides are excellent candidates for vaccines and diagnostics.

The intracellularly produced, truncated E1 and E2 polypeptides can be obtained using a variety of techniques. For example, the polypeptides can be generated using recombinant techniques, well known in the art. In this regard, oligonucleotide probes can be devised based on the known sequences of the HCV genome and used to probe genomic or cDNA libraries for E1 and E2 genes. The genes can then be further isolated using standard techniques and, e.g., restriction enzymes employed to truncate the gene at desired portions of the full-length sequence. Similarly, the E1 and E2 genes can be isolated directly from cells and tissues containing the same, using known techniques, such as phenol extraction and the sequence further manipulated to produce the desired truncations. See, e.g., Sambrook et al., supra, for a description of techniques used to obtain and isolate DNA. Finally, the genes encoding the truncated E1 and E2 polypeptides can be produced synthetically, based on the known sequences. The nucleotide sequence can be designed with the appropriate codons for the particular amino acid sequence desired. In general, one will select preferred codons for the intended host in which the sequence will be expressed. The complete sequence is generally assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) *J. Biol. Chem.* 259:6311.

Once coding sequences for the desired proteins have been isolated or synthesized, they can be cloned into any suitable vector or replicon for expression. Numerous cloning vectors are known to those of skill in the art, and the selection of an appropriate cloning vector is a matter of choice. Examples of recombinant DNA vectors for cloning and host cells which they can transform include the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (Bacillus), pIJ61 (Streptomyces), pUC6 (Streptomyces), YIp5 (Saccharomyces), YCp19 (Saccharomyces) and bovine papilloma virus (mammalian cells). See, generally, *DNA Cloning*: Vols. I & II, supra; Sambrook et al., supra; B. Perbal, supra.

Insect cell expression systems, such as baculovirus systems, can also be used and are known to those of skill in the art and described in, e.g., Summers and Smith, *Texas Agricultural Experiment Station Bulletin No.* 1555 (1987). Materials and methods for baculovirus/insect cell expression systems are commercially available in kit form from, inter alia, Invitrogen, San Diego Calif. ("MaxBac" kit).

Plant expression systems can also be used to produce the truncated E1 and E2 proteins. Generally, such systems use virus-based vectors to transfect plant cells with heterologous genes. For a description of such systems see, e.g., Porta et al., *Mol. Biotech.* (1996) 5:209–221; and Hackiand et al., *Arch. Virol.* (1994) 139:1–22.

Viral systems, such as a vaccinia based infection/transfection system, as described in Tomei et al., *J. Virol.* (1993) 67:4017–4026 and Selby et al., *J. Gen. Virol.* (1993) 74:1103–1113, will also find use with the present invention. In this system, cells are first transfected in vitro with a vaccinia virus recombinant that encodes the bacteriophage T7 RNA polymerase. This polymerase displays exquisite specificity in that it only transcribes templates bearing T7 promoters. Following infection, cells are transfected with the DNA of interest, driven by a T7 promoter. The polymerase expressed in the cytoplasm from the vaccinia virus recombinant transcribes the transfected DNA into RNA which is then translated into protein by the host translational machinery. The method provides for high level, transient, cytoplasmic production of large quantities of RNA and its translation product(s).

The gene can be placed under the control of a promoter, ribosome binding site (for bacterial expression) and, optionally, an operator (collectively referred to herein as "control" elements), so that the DNA sequence encoding the desired E1 or E2 polypeptide is transcribed into RNA in the host cell transformed by a vector containing this expression construction. The coding sequence may or may not contain a signal peptide or leader sequence. With the present invention, both the naturally occurring signal peptides or heterologous sequences can be used. Leader sequences can be removed by the host in post-translational processing. See, e.g., U.S. Pat. Nos. 4,431,739; 4,425,437; 4,338,397. Such sequences include, but are not limited to, the tpa leader, as well as the honey bee mellitin signal sequence.

Other regulatory sequences may also be desirable which allow for regulation of expression of the protein sequences relative to the growth of the host cell. Such regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector. Alternatively, the coding sequence can be cloned directly into an expression vector which already contains the control sequences and an appropriate restriction site.

In some cases it may be necessary to modify the coding sequence so that it may be attached to the control sequences with the appropriate orientation; i.e., to maintain the proper reading frame. It may also be desirable to produce mutants or analogs of the E1 or E2 protein. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., Sambrook et al., supra; *DNA Cloning*, Vols. I and II, supra; *Nucleic Acid Hybridization*, supra.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), as well as others. Similarly, bacterial hosts such as *E. coli, Bacillus subtilis*, and Streptococcus spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda,* and *Trichoplusia ni*.

Depending on the expression system and host selected, the proteins of the present invention are produced by growing host cells transformed by an expression vector described above under conditions whereby the protein of interest is expressed. The selection of the appropriate growth conditions is within the skill of the art. The cells are then disrupted, using chemical, physical or mechanical means, which lyse the cells yet keep the HCV polypeptides substantially intact. Intracellular proteins can also be obtained by removing components from the cell wall or membrane, e.g., by the use of detergents or organic solvents, such that leakage of the E1 and/or E2 polypeptides occurs. Such methods are known to those of skill in the art and are described in, e.g., *Protein Purification Applications: A Practical Approach*, (E. L. V. Harris and S. Angal, Eds., 1990)

For example, methods of disrupting cells for use with the present invention include but are not limited to: sonication or ultrasonication; agitation; liquid or solid extrusion; heat treatment; freeze-thaw; desiccation; explosive decompression; osmotic shock; treatment with lytic enzymes including proteases such as trypsin, neuraminidase and lysozyme; alkali treatment; and the use of detergents and solvents such as bile salts, sodium dodecylsulphate, Triton, NP40 and CHAPS. The particular technique used to disrupt the cells is largely a matter of choice and will depend on the cell type in which the polypeptide is expressed, culture conditions and any pre-treatment used.

Following disruption of the cells, cellular debris is removed, generally by centrifugation, and the intracellularly produced E1 and/or E2 polypeptides are further purified, using standard purification techniques such as but not limited to, column chromatography, ion-exchange chromatography, size-exclusion chromatography, electrophoresis, HPLC, immunoadsorbent techniques, affinity chromatography, immunoprecipitation, and the like.

For example, one method for obtaining the intracellular HCV polypeptides of the present invention involves affinity purification, such as by immunoaffinity chromatography using anti-E1 and/or anti-E2 specific antibodies, or by lectin affinity chromatography. Particularly preferred lectin resins are those that recognize mannose moieties such as but not limited to resins derived from *Galanthus nivalis* agglutinin (GNA), *Lens culinaris* agglutinin (LCA or lentil lectin), *Pisum sativum* agglutinin (PSA or pea lectin), *Narcissus pseudonarcissus* agglutinin (NPA) and *Allium ursinum* agglutinin (AUA). The choice of a suitable affinity resin is within the skill in the art. After affinity purification, the E1 and E2 polypeptides can be further purified using conventional techniques well known in the art, such as by any of the techniques described above.

It may be desirable to produce E1/E2 complexes. Such complexes are readily produced by e.g., co-transfecting host cells with constructs encoding for the E1 and E2 truncated proteins. Co-transfection can be accomplished either in trans or cis, i.e., by using separate vectors or by using a single vector which bears both of the E1 and E2 genes. If done using a single vector, both genes can be driven by a single set of control elements or, alternatively, the genes can be present on the vector in individual expression cassettes, driven by individual control elements. Following expression, the E1 and E2 proteins will spontaneously associate. Alternatively, the complexes can be formed by mixing the individual proteins together which have been produced separately, either in purified or semi-purified form, or even by mixing culture media in which host cells expressing the proteins, have been cultured. See, International Publication No. WO 96/04301, published Feb. 15, 1996, for a description of such complexes.

The intracellularly produced E1 and E2 polypeptides of the present invention, complexes thereof, or the polynucleotides coding therefor, can be used for a number of diagnostic and therapeutic purposes. For example, the proteins and polynucleotides or antibodies generated against the same, can be used in a variety of assays, to determine the presence of reactive antibodies/and or E1 and E2 proteins in a biological sample to aid in the diagnosis of HCV disease.

The presence of antibodies reactive with the HCV polypeptides and, conversely, antigens reactive with antibodies generated thereto, can be detected using standard electrophoretic and immunodiagnostic techniques, including immunoassays such as competition, direct reaction, or sandwich type assays. Such assays include, but are not limited to, western blots; agglutination tests; enzyme-labeled and mediated immunoassays, such as ELISAs; biotin/avidin type assays; radioimmunoassays; immunoelectrophoresis; immunoprecipitation, etc. The reactions generally include revealing labels such as fluorescent, chemiluminescent, radioactive, or enzymatic labels or dye molecules, or other methods tor detecting the formation of a complex between the antigen and the antibody or antibodies reacted therewith.

Solid supports can be used in the assays such as nitrocellulose, in membrane or microtiter well form; polyvinylchloride, in sheets or microtiter wells; polystyrene latex, in beads or microtiter plates; polyvinylidine fluoride; diazotized paper; nylon membranes; activated beads, and the like.

Typically, the solid support is first reacted with the biological sample (or the E1 and/or E2 proteins), washed and then the antibodies, (or a sample suspected of containing antibodies), applied. After washing to remove any non-bound ligand, a secondary binder moiety is added under suitable binding conditions, such that the secondary binder is capable of associating selectively with the bound ligand. The presence of the secondary binder can then be detected using techniques well known in the art. Typically, the secondary binder will comprise an antibody directed against the antibody ligands. A number of anti-human immunoglobulin (Ig) molecules are known in the art (e.g., commercially available goat anti-human Ig or rabbit anti-human Ig). Ig molecules for use herein will preferably be of the IgG or IgA type, however, IgM may also be appropriate in some instances. The Ig molecules can be readily conjugated to a detectable enzyme label, such as horseradish peroxidase, glucose oxidase, Beta-galactosidase, alkaline phosphatase and urease, among others, using methods known to those of skill in the art. An appropriate enzyme substrate is then used to generate a detectable signal.

Alternatively, a "two antibody sandwich" assay can be used to detect the proteins of the present invention. In this technique, the solid support is reacted first with one or more of the antibodies directed against E1 and/or E2, washed and then exposed to the test sample. Antibodies are again added and the reaction visualized using either a direct color reaction or using a labeled second antibody, such as an anti-immunoglobulin labeled with horseradish peroxidase, alkaline phosphatase or urease.

Assays can also be conducted in solution, such that the viral proteins and antibodies thereto form complexes under precipitating conditions. The precipitated complexes can then be separated from the test sample, for example, by centrifugation. The reaction mixture can be analyzed to determine the presence or absence of antibody-antigen complexes using any of a number of standard methods, such as those immunodiagnostic methods described above.

The E1 and/or E2 proteins, produced as described above, or antibodies to the proteins, can be provided in kits, with suitable instructions and other necessary reagents, in order to conduct immunoassays as described above. The kit can also contain, depending on the particular immunoassay used, suitable labels and other packaged reagents and materials (i.e. wash buffers and the like). Standard immunoassays, such as those described above, can be conducted using these kits.

The E1 and E2 polypeptides and polynucleotides encoding the polypeptides can also be used in vaccine compositions, individually or in combination, in e.g., prophylactic (i.e., to prevent infection) or therapeutic (to treat HCV following infection) vaccines. The vaccines can comprise. mixtures of one or more of the E1 and E2 proteins (or nucleotide sequences encoding the proteins), such as E1 and E2 proteins derived from more than one viral isolate. The vaccine may also be administered in conjunction with other antigens and immunoregulatory agents, for example, immunoglobulins, cytokines, lymphokines, and chemokines, including but not limited to IL-2, modified IL-2 (cys125→ser125), GM-CSF, IL-12, γ-interferon, IP-10, MIP1β and RANTES.

The vaccines will generally include one or more "pharmaceutically acceptable excipients or vehicles" such as water, saline, glycerol, ethanol, etc. Additionally, auxiliary substances, such as wetting or emulsifying agents, pH buffering substances, and the like, may be present in such vehicles.

A carrier is optionally present which is a molecule that does not itself induce the production of antibodies harmful to the individual receiving the composition. Suitable carriers are typically large, slowly metabolized macromolecules such as proteins, polysaccharides, polylactic acids, polyglycollic acids, polymeric amino acids, amino acid copolymers, lipid aggregates (such as oil droplets or liposomes), and inactive virus particles. Such carriers are well known to those of ordinary skill in the art. Furthermore, the HCV polypeptide may be conjugated to a bacterial toxoid, such as toxoid from diphtheria, tetanus, cholera, etc.

Adjuvants may also be used to enhance the effectiveness of the vaccines. Such adjuvants include, but are not limited to: (1) aluminum salts (alum), such as aluminum hydroxide, aluminum phosphate, aluminum sulfate, etc.; (2) oil-in-water emulsion formulations (with or without other specific immunostimulating agents such as muramyl peptides (see below) or bacterial cell wall components), such as for example (a) MF59 (International Publication No. WO 90/14837), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, MT) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+ CWS (Detox™); (3) saponin adjuvants, such as Stimulon™ (Cambridge Bioscience, Worcester, Mass.) may be used or particle generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2, etc.), macrophage colony stimulating factor (M-CSF), tumor necrosis factor (TNF), etc.; (6) detoxified mutants of a bacterial ADP-ribosylating toxin such as a cholera toxin (CT), a pertussis toxin (PT), or an E. coli heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (see, e.g., International Publication Nos. W093/13202 and W092/19265); and (7) other substances that act as immunostimulating agents to enhance the effectiveness of the composition.

Muramyl peptides include, but are not limited to, N-acetyl-muramyl-L-threonyl-D-isoglutamine (thr-MDP), N-acteyl-normuramyl-L-alanyl-D-isogluatme (nor-MDP), N-acetylmuramyl-L-alanyl-D-isogluatminyl-L-alanine-2-(1'-2'-dipalmitoyl-sn-glycero-3-huydroxyphosphoryloxy)-ethylamine (MTP-PE), etc.

Typically, the vaccine compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above.

The vaccines will comprise a therapeutically effective amount of the E1 and/or E2 truncated proteins, or complexes of the proteins, or nucleotide sequences encoding the same, and any other of the above-mentioned components, as needed. By "therapeutically effective amount" is meant an amount of an E1 and/or E2 truncated protein which will induce a protective immunological response in the individual to which it is administered. Such a response will generally result in the development in the subject of a secretory, cellular and/or antibody-mediated immune response to the vaccine. Usually, such a response includes but is not limited to one or more of the following effects; the production of antibodies from any of the immunological classes, such as immunoglobulins A, D, E, G or M; the proliferation of B and T lymphocytes; the provision of activation, growth and differentiation signals to immunological cells; expansion of helper T cell, suppressor T cell, and/or cytotoxic T cell and/or γδ T cell populations.

Preferably, the effective amount is sufficient to bring about treatment or prevention of disease symptoms. The exact amount necessary will vary depending on the subject being treated; the age and general condition of the individual to be treated; the capacity of the individual's immune system to synthesize antibodies; the degree of protection desired; the severity of the condition being treated; the particular HCV polypeptide selected and its mode of administration, among other factors. An appropriate effective amount can be readily determined by one of skill in the art. A "therapeutically effective amount" will fall in a relatively broad range that can be determined through routine trials.

Once formulated, the vaccines are conventionally administered parenterally, e.g., by injection, either subcutaneously or intramuscularly. Additional formulations suitable for other modes of administration include oral and pulmonary formulations, suppositories, and transdermal applications. Dosage treatment may be a single dose schedule or a multiple dose schedule. The vaccine may be administered in conjunction with other immunoregulatory agents.

III. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Materials and Methods

HCV Templates

Figure 4:
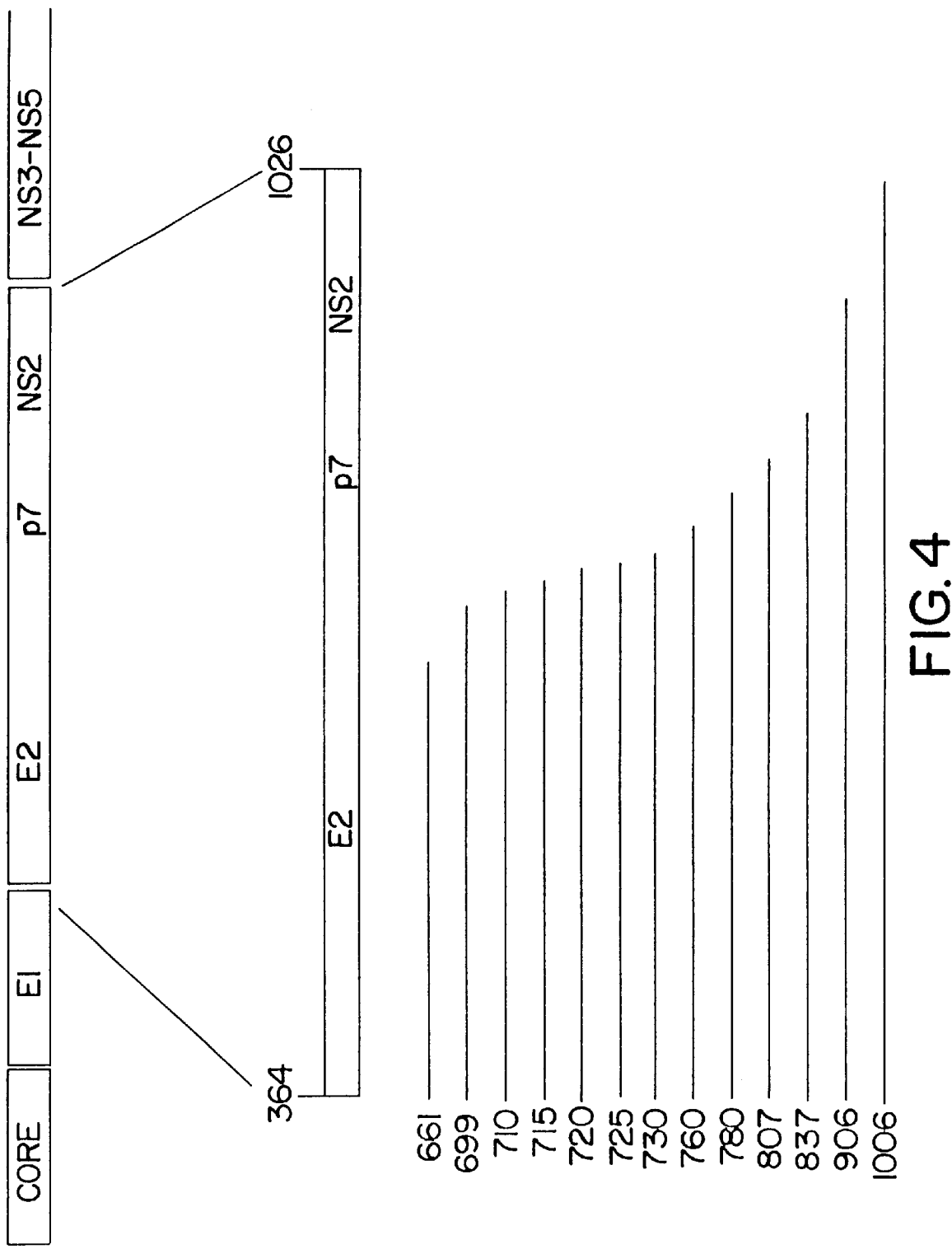
FIG. 4 depicts some of the HCV E2 cDNA templates described in the Examples. The core through NS2 region is shown on the top and is drawn to scale; the distal NS3 through NS5 is not drawn to scale. The E2/NS2 region has been expanded to better display the various templates. The column to the left refers to the amino acid endpoint used in each template.

A series of truncated E1 templates, shown in FIG. 3, and E2 templates, shown in FIG. 4, were generated using PCR. The appropriate 5' primer containing a methionine residue and an NcoI site was used along with 3' primers that had a termination codon following the designated envelope endpoint and finally, for E1, a BamHI site. Both oligos had non-specific sequences on the ends to facilitate more efficient digestions by NcoI and BamHI enzymes. Digested PCR fragments were ligated into NcoI/BamHI-digested pTM1 (Elroy-Stein and Moss, *Proc. Natl. Acad. Sci. USA* (1990) 87:6743–6747). The pTM1 vector contains the T7 promoter and the EMC leader proximal to the NcoI cloning site which corresponds to the first methionine residue encoded by the designated DNA. E2 templates were digested with NcoI and AscI and cloned into NcoI(partial)/ AscI-pTM1-CE2 (Selby et al., *J. Gen. Virol.* (1993) 74:1103–1113) to generate the H clones where translations began at amino acid 1 and encode core, E1 and the designated E2 regions.

For the truncated E1 polypeptides, coding templates began with a methionine residue, followed by isoleucine and then amino acid 172. In particular, coding templates beginning with a methionine residue, followed by isoleucine and then amino acid 172 of the HCV polyprotein and continuing to amino acid 330, and clones of 10 amino acid increments through amino acid 380, were generated. Amino acids 173 through 191 correspond to the C-terminus of core which apparently serves a role as a signal sequence. Mature E1 is thought to begin at amino acid 192 of the polyprotein following signal sequence cleavage.

For the truncated E2 constructs, the methionine at position 364 was used as the N-terminus in the constructions. Amino acid 364 corresponds to the approximate start of the E2 signal peptide (Hijikata et al., *Proc. Natl. Acad. Sci. USA* (1991) 88:5547–5551; Ralston et al., *J. Virol.* (1993) 67:6753–6761). Mature E2 is thought to begin with amino acid 385. The staggered C-termini ranged from amino acid 661 through 1006. In particular, the clones terminated at amino acids 661, 699, 710, 715, 720, 725, 730, 760, 780, 807, 837, 906 and 1006.

In addition to those clones described above and shown in FIG. 4, truncated E2 polypeptides, terminating at amino acids 500, 550, 590, 625, 655, and a construct terminating at amino acid 715 and including an additional deletion of the N-terminal hypervariable region, termed δ715, were also made as described above.

Intracellular Production of Truncated HCV E2

A truncated E2 molecule was expressed which had its C-terminus at amino acid $715_{lys}$ ("$E2_{715}$") as follows. A clone terminating at amino acid 715 was used to transfect a DHFR-deficient Chinese hamster ovary (CHO) cell line using techniques described in Spaete et al., *Virol.* (1992) 188:819–830. Following expression, CHO cells were lysed and the intracellularly produced $E2_{715}$ was purified by GNA agarose chromatography, followed by cation-exchange chromatography, as follows.

To lyse the cells, two volumes of lysis buffer (4% Triton X-100 in 0.1M Tris pH8, 1 mM EDTA, 1 μg/ml pepstatin A and 1 mM phenylmethyl-sulfonyl fluoride (PMSF)) were added to the CHO cells at 4° C. The mixture was homogenized in aliquots in a 40 ml Dounce homogenizer using tight-fit pestle B (20 strokes). The homogenate was spun at 12 K rpm for 20 min at 4° C. The supernatant was adjusted with water to 2% Triton/50 mM Tris pH8 and homogenized again using pestle B (10 strokes). The homogenate was spun as above and the intracellularly produced $E2_{715}$ further purified from the supernatant as follows.

A GNA agarose column (4 ml bed volume, vector Labs, Burlingame, Calif.) was pre-equilibrated with detergent buffer (2% Triton/50 mM Tris pH8). The supernatant sample was applied to the column at 4° C. and the column was washed with 5 bed-volumes of column buffer (0.1% Triton/ 20 mM sodium phosphate pH6). The column was also washed with 5 bed-volumes of 1M NaCl. (Alternatively, the NaCl can be added to the detergent buffer to a concentration of 1M prior to loading the sample unto the column.) The E2 protein was eluted in 5 bed-volumes of methyl α-D-mannopyranoside (MMP) and 1M NaCl and 1.2 ml fractions collected.

Fractions containing the E2 protein were pooled and diluted with 2 volumes of S-Sepharose buffer (0.1% Triton/ 20 mM sodium phosphate pH6). The pooled and diluted fractions were membrane-dialysed (Spectra/Por, molecular weight cut-off 1,000) against 4 L of S-Sepharse buffer overnight at 4° C. with constant stirring. Following dialysis, the dialysate was applied to an S-Sepharose column (fast flow, Pharmacia, 4° C., 4 ml bed-volume, pre-equilibrated in S-Sepharose buffer). The column was washed in 5 bed-volumes of S-Sepharose buffer and 1 ml fractions eluted in 0.5M NaCl in S-Sepharose buffer. Fractions containing E2 were pooled and the column was washed with 1M NaCl in S-Sepharose buffer and re-equilibrate in S-Sepharose buffer.

E2 polypeptide δ715 (described above), as well as the E2 molecules terminating at amino acids 500, 550, 590, 625 and 655 were also produced as described above.

Production of Secreted, Truncated HCV E2

A truncated E2 molecule was made which had its C-terminus at amino acid $715_{lys}$ ("$E2_{715}$"). The truncated E2 molecule was expressed using a Chinese hamster ovary cell/dihydrofolate reductase (CHO/DHFR) expression system as described in Spaete et al., Virol. (1992) 188:819–830. Following expression, secreted $E2_{715}$ was purified for use in further experiments as described in International Publication No. WO 96/04301, published Feb. 15, 1996.

E2 polypeptide δ715 (described above), as well as the E2 molecules terminating at amino acids 500, 550, 590, 625 and 655 were also produced as described above.

Intracellular Production of E1/E2 Complex

An E1/E2 complex, including complexed full-length E1 and E2, produced in HeLa cells, was isolated as follows. HeLa S3 cells were inoculated with purified high-titer vaccinia virus that expressed E1 and E2 at a multiplicity of infection of 5 pfu/cell, and the mixture was stirred at 37° C. for 30 minutes. The infected cells were then transferred to a spinner flask containing 8 liters spinner medium and incubated for 3 days at 37° C. The cells were collected again by centrifugation and resuspended in hypotonic buffer (20 mM HEPES, 10 mM NaCl, 1 mM NaCl, 1 mM $MgCl_2$, 120 ml) on ice.

Following expression, HeLa cells were lysed with Triton X-100 and E1/E2 was isolated by GNA agarose chromatography followed by cation-exchange chromatography using the procedure used to purify the intracellularly expressed E2. The resulting material was provided in buffer containing 0.05% Triton X-100. Reducing SDS-PAGE analysis showed it to have a relatively tight 55 kD band consistent with the presence of a large amount of mannose-type glycosylation. Purity was estimated at 33%. The complex was used as a control in the following experiments.

EXAMPLE 1

Receptor Binding of Secreted and Intracellular E2

The GNA agarose-purified intracellular E2, and secreted E2, were used in binding assays as described in Rosa et al., Proc. Natl. Acad. Sci. USA (1996) 93:1759–1763 and International Publication No. WO 96/05513, published Feb. 22, 1996. This assay assesses specific binding of the E2 proteins to human lymphoma T-cells (MOLT-4 cells) and the neutralization thereof, based on the cytofluorimetric assessment of sera that neutralize the binding of the antigens to the MOLT-4 cells.

Figure 5:
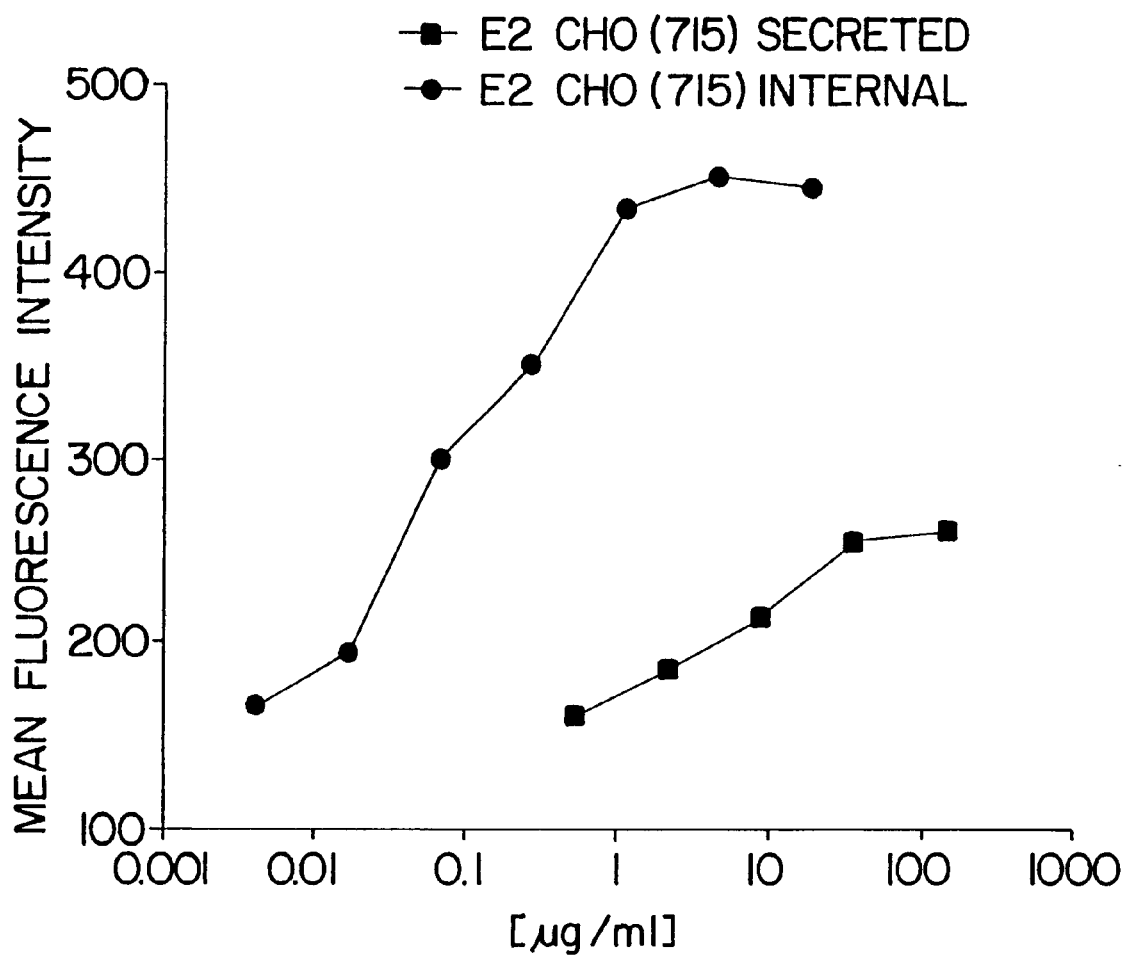
FIG. 5 depicts the results of a neutralization of binding assay performed with secreted, truncated E2 and intracellularly produced (internal), truncated E2.

As shown in FIG. 5, the intracellular (internal) E2 bound to the cells approximately 30-fold more efficiently than the secreted counterpart.

EXAMPLE 2

Immunoreactivity of Secreted and Intracellular E2

The immunoreactivity of the intracellularly produced truncated E2 protein was also compared to that of the secreted E2 protein using mouse monoclonal antibodies and human polyclonal sera.

A. Epitope Exposure Study of Intracellular and Secreted E2 Using Anti-E2 Monoclonal Antibodies Mouse monoclonal antibodies used in the assays were produced as follows. Mice were immunized with the immunogen specified in Table 1. Spleen cells from immunized mice were obtained and fused with $2.5 \times 10^7$ NSO/2 mouse myeloma cells in 50% polyethylene glycol 4000 (Merck) using the procedure described by Kohler and Milstein, Nature (1975) 256:495–497. After the fusion, the cells were resuspended in HAT made with Dulbecco's medium, supplemented with nonessential amino acids, 10% fetal bovine serum (FBS) (Hyclone Laboratories, Salt Lake City, Utah) 100 Ul/ml of penicillin, 100 μg/ml streptomycin, 2mM L-glutamine, $10^8$M hypoxanthine, $4 \times 10^{-3}$M thymidine (all reagents from Sigma). Aliquots of 100 μl were seeded on 96-well tissue culture plates (Nunc, DK 4000 Roskikle, Denmark). The plates were incubated at 37° C. in moisturized atmosphere with 10% $Co_2$ in air. Ten days after fusion, supernatants from cultures exhibiting hybridoma growth were screened by hemagglutination for the production of anti-B antibodies. All positive cultures were expanded to 24-well plates and the cells were frozen under liquid nitrogen in a medium containing 90% (FCS and 10% dimethylsulfoxide (Merck). Hybridomas of interest were selected on the basis of their specificity, avidity, and intensity of the agglutination reaction and recloned twice by the limiting dilution technique.

To induce ascitic fluid, the recloned hybridomas were grown in the peritoneal cavity of BALB/C or $F_2$, (BALB/C×B10) mice, previously injected intraperitoneally with 0.5 ml of 2,6,10,14-tetramethylpenindecane (Pristane, from Sigma).

Isotypes of the antibodies were determined with a commercial kit, based on agglutination of sheep red blood cells coupled with rat monoclonal antibodies against mouse immunoglobulin isotype (Serotec, 22 Bankside, Oxford, England). The isotype, specificity and characterization of the monoclonal antibodies is shown in Table 1.

TABLE 1

HCV Monoclonal Antibodies List

| Mab ID# | Isotype | Specificity | Characterization | Immunogen |
|---|---|---|---|---|
| 5E5/H7 | IgG1 | anti-HCV e2 | Conformational Ab | HeLa e1/e2 (aa 1–967) |
| 2A3/B12 | ND | anti-HCV e2 | Conformational Ab | HeLa e1/e2 (aa 1–967) |
| 5E9/D10 | ND | anti-HCV e2 | Conformational Ab | HeLa e1/e2 (aa 1–967) |
| 3F5/H6 | ND | anti-HCV e2 | Conformational Ab | HeLa e1/e2 (aa 1–967) |
| 3D5/C3 | IgG1 | anti-HCV e2 | Anti-linear epitope Ab | HeLa e1/e2 (aa 1–967) |
| 3E5-1 | IgG1 | anti-HCV e2 | Anti-linear epitope Ab | Insect e2 (aa 404–661) |
| The conformational anti-e2 Mabs titers: | | | | |
| 3E5/H7 > 3F5/H6 > 5E9/D10 > B12 | | | | |
| 472.2–5 | ND | anti-HCV e2 | Anti-hypervariable region | e2 HV peptide |
| 6A1 | IgG1 | anti-HCV e2 | Conformational Ab (blocks binding to MOLT4 receptor) | CHO e1/e2 (aa 1–967) |

TABLE 1-continued

HCV Monoclonal Antibodies List

| Mab ID# | Isotype | Specificity | Characterization | Immunogen |
|---|---|---|---|---|
| 6A21 | IgG1 | anti-HCV e2 | Conformational Ab (blocks binding to MOLT4 receptor) | |

Epitope exposure of the secreted and intracellularly produced E2 proteins was determined using the monoclonal antibodies above as follows. Costar high-binding plates were loaded with 200 µl of purified E2 antigen (200 ng/well), as described in Table 2, which had been diluted in coating buffer. Plates were incubated overnight at room temperature and then washed 3 times with $dH_2O$. The plates were post coated with 300 µl of post coat solution and incubated for 1 hour at room temperature. Plates were aspirated and 300 µl of stability solution added to the plate. Plates were incubated for 1 hour at room temperature, aspirated and tapped several times. The plates were dried in a lyophilizer for at least 4 hours.

200 µl of prediluted (1:100) monoclonal antibodies, specified in Table 2, were added to the plates and the plates were incubated at 37° C. for 1 hour. The plates were washed 5 times with wash buffer and 200 µl of 1:5 K conjugate goat anti-mouse IgG (H+L) Fab'2, added. Plates were incubated at 37° C. for 1 hour and washed as above. The plates were developed using 200 µl of OPD Substrate. The results are shown in Table 2. As can be seen, the secreted E2 protein was only recognized by a monoclonal antibody against a linear epitope whereas the intracellularly (internal) produced E2 was recognized by monoclonal antibodies against both linear and conformational epitopes.

TABLE 2

Evaluation of Epitope Exposure by Murine Anti-E2 Monoclonal Antibodies

| | Anti-E1 Mab NC 3D5/C3 | Anti-E2 Mab Linear Epitope 3E5-1 | Anti-E2 Mab Conformational Epitope 5E5/H7 | Anti-E2 Mab Conformational Epitope 3F5/H6 | Anti-E2 Mab Neutralizing Epitope 6A21 |
|---|---|---|---|---|---|
| Internal CHOE2 (50%) | 0.004 | 1.923 | 0.496 | 0.391 | 0.355 |
| Secreted CHOE2 Dimer (80% Pure) | 0.000 | 1.392 | 0.037 | 0.025 | 0.009 |
| Secreted CHOE2 | 0.007 | 1.833 | 0.161 | 0.115 | 0.140 |
| Monomer/Dimer (60% Pure) | 0.001 | 1.605 | 0.122 | 0.067 | 0.051 |

NC = Negative control
Cut off = 0.350 OD

B. Immunoreactivity Study of Secreted and Intracellular E2 Using HCV Serconversion In order to further determine the immunoreactivity of intracellularly produced truncated E2 versus the secreted E2, seroconversion panels were run using a commercial source of sera. 5 µl of each serum sample, diluted in 200 µl of sample diluent, were added to plates, prepared as described above, using the antigens identified in Table 3. The plates were incubated at 37° C. for 1 hour and washed 5 times with wash buffer. 200 µl of conjugate goat anti-human IgG (H+L) Fab'2, diluted in conjugate diluent, was added and plates were incubated at 37° C. for 1 hour. Plates were washed as above and developed using 200 µl of OPD Substrate.

TABLE 3

Evaluation of E2 ELISA Assay Sensitivity by Testing HCV Seroconversion Panel

| Sample | Internal CHOE2 50% Pure OD | Secreted CHOE2 Dimer (80% Pure) OD | Secreted CHOE2 Monomer/Dimer (60% Pure) OD |
|---|---|---|---|
| PHV904-01 | 0.032 | 0.026 | 0.020 |
| PHV904-02 | 0.040 | 0.041 | 0.028 |
| PHV904-03 | 0.109 | 0.017 | 0.019 |
| PHV904-04 | 0.505 | 0.048 | 0.029 |
| PHV904-05 | 1.681 | 0.268 | 0.158 |

TABLE 3-continued

Evaluation of E2 ELISA Assay Sensitivity by
Testing HCV Seroconversion Panel

| Sample | Internal CHOE2 50% Pure OD | Secreted CHOE2 Dimer (80% Pure) OD | Secreted CHOE2 Monomer/Dimer (60% Pure) OD |
|---|---|---|---|
| PHV904-06 | 1.095 | 0.152 | 0.082 |
| PHV904-07 | 0.987 | 0.105 | 0.063 |

The intracellular E2 was significantly more sensitive than any of the secreted E2 proteins in detecting seroconversion. See, e.g., Table 3 which details the results from a typical assay.

The above results indicate that the intracellularly produced truncated E2 protein is more immunoreactive than the secreted counterpart. Thus, intracellular protein provides a better diagnostic reagent due to the enhanced immunoreactivity.

C. Immunoreactivity Study of Secreted and Intracellular E2 Using Immobilized HCV Antibodies In order to further determine the immunoreactivity of intracellularly produced truncated E2 versus the secreted E2, further studies were conducted using immobilized HCV antibodies. Antibodies used in these assays were monoclonal antibodies 6A21 and 3E5-1, both described in Table 1 above, as well as an IgG antibody preparation purified from serum of an HCV-infected patient, and specific for the hypervariable region at the N-terminus of E2.

In particular, antibody FF25931 was purified from patient serum through a Protein G affinity column and then conjugated to paramagnetic particles (Chiron Diagnostics, Walpole, Mass.) prior to use in the assays. Monoclonal antibodies 6A21 and 3E5-1 were also Protein G purified through a 5 ml gel (Pierce, Rockford, Ill.) and the antibodies covalently linked to magnetic latex particles (Bangs Laboratories, Fisher, Ind.) using 1-ethyl-3-C3-dimethylaminopropyl carbodimide hydrochloride (EDC) chemistry.

The detection reagent used in the assays was guinea pig polyclonal antisera raised against secreted $E2_{715}$, produced as described above. 1 ml of the polyclonal antisera was purified by passage through a 1 ml gel Protein A column (Pierce). Protein content was determined by reading absorbance at 280 nm. The antibody was labeled with 2',6'-dimethyl-4'-(N-succinimidyloxycarboxnyl)phenyl-10-(3'-sulfopropyl)-acridinium-9-carboxylate (NHS-NSP-DMAE) (Chiron Diagnostics, Walpole, Mass.).

Both the solid-phase antibodies and the detection reagent were optimized and diluted in working buffer (50 mM Tris pH 8.0, 500 mM KCl, 1 mM EDTA, 1.75% BSA, 0.01% Tween-20).

Assays were conducted as follows. 100 µl sample were placed in a 75×12 mm polystyrene tube (Sarstedt, Newton, N.C.) and 100 µl of the solid-phase antibody added at 30 µg/assay. This was incubated at 37° C. for 18 minutes. 100 µl of the detection reagent was added in an amount of $30 \times 10^6$ relative light units (RLUs) per assay and the reaction allowed to proceed for 18 minutes at 37° C. The product was washed three times with phosphate bufferred saline, 0.1% Tween-20 and tubes were read using a Magic Lite Analyzer II (Chiron Diagnostics, Walpole, Mass.). Results are shown in Table 4.

The assay was repeated using the FF25931 antibody, immobilized on paramagnetic particles, as described above and detection was accomplished using monoclonal antibody 1G2/A7, specific for the hypervariable region at the N-terminus of E2, conjugated to NHS-NSP-DMAE. Results of this assay are shown in Table 5.

As can be seen in Table 4, monoclonal antibody 3E5-1 reacts with E2 truncations terminating at amino acid 550 and higher, both in supernatants (media) as well as the intracellular lysates. However, the 6A21 monoclonal antibody which blocks binding of E2 in the Molt-4 NOB assay, does not bind to E2 truncations terminating between 500 and 625. There is substantial immunoreactivity with molecules terminating at amino acid 655 and higher. Thus, it appears that residues below 655 are required for the E2 to assume the right structure to bind to 6A21. E2 terminating at 661 also has high reactivity to 6A21, but E2 terminating at 715 has a substantially lower immunoreactivity to 6A21. This effect is particularly seen in supernatant.

As shown in Tables 4 and 5, the same effect is seen with antibody FF25931, an antibody specific to the hypervariable region at the N-terminus of E2. Truncations at 625, 655 and 661 were very active, but there was a drop with $E2_{715}$ both in the supernatant and in the media. The $\delta 715$ molecules were substantially inactive with all antibodies tested.

The data show that $E2_{655}$ and $E2_{661}$ are considerably immunoreactive.

TABLE 4

| Solid Phase Antibody: | 3E5-1 | 6A21 | FF25931 |
|---|---|---|---|
|  | supernatant | supernatant | supernatant |
| control | 1047 | 1093 | 1771 |
| 500 | 1232 | 955 | 18033 |
| 550 | 1138476 | 1109 | 4682 |
| 590 | 1015661 | 955 | 4820 |
| 625 | 991775 | 1109 | 5282 |
| 655 | 775221 | 12043 | 99037 |
| 661 | 740509 | 10980 | 88920 |
| 715 | 764918 | 2803 | 29044 |
| δ715 | 1032 | 1032 | 1602 |
|  | lysate | lysate | lysate |
| control | 2449 | 1186 | 2726 |
| 500 | 1525 | 1078 | 5144 |
| 550 | 531177 | 1309 | 2618 |
| 590 | 480264 | 1324 | 2325 |
| 625 | 393624 | 1971 | 2110 |
| 655 | 389743 | 5421 | 58797 |
| 661 | 400492 | 6283 | 64141 |
| 715 | 492492 | 2356 | 22453 |
| δ715 | 1571 | 1386 | 1771 |

TABLE 5

| Solid Phase Antibody: | FF25931 |
|---|---|
| | supernatant |
| control | 2079 |
| 500 | 53623 |
| 550 | 9948 |
| 590 | 9748 |
| 625 | 11689 |
| 655 | 261589 |
| 661 | 204959 |
| | lysate |
| control | 2911 |
| 500 | 8778 |
| 550 | 4389 |
| 590 | 3388 |
| 625 | 7069 |
| 655 | 212166 |
| 661 | 148749 |

EXAMPLE 3

Immunization of Guinea Pigs with Secreted and Intracellular E2

The immunogenicity of secreted and intracellularly produced HCV $E2_{715}$ was determined in guinea pigs. Five groups of animals were immunized with the antigens described above, formulated with MF-75 and MTP-PE as an adjuvant. The internal HeLa E1/E2 was used as a control E2 preparation. Guinea pigs were immunized IM at 0, 1 and 3 months with doses specified in Table 6, and sera from the guinea pigs was collected and pooled for further study.

TABLE 6

E2 Preps and doses used to immunize guinea pigs.

| E2 Prep | Group # | Dose[a] |
|---|---|---|
| Internal CHO E2 | 5 | 80 μg |
| | 6 | 8.0 μg |
| | 7 | 0.8 μg |
| | 8 | 8.0, 2.0, 0.8 μg |
| Secreted CHO E2 | 9 | 80 μg |
| | 10 | 8.0 μg |
| | 11 | 0.8 μg |
| | 12 | 8.0, 2.0, 0.8 μg |

TABLE 6-continued

E2 Preps and doses used to immunize guinea pigs.

| E2 Prep | Group # | Dose[a] |
|---|---|---|
| HeLa Internal E1/E2 | 16 | 8.0, 2.0, 0.8 μg |

[a]diluted in MF75-0 containing 50 μg MTP-PE for the first dose and 10 μg for subsequent doses on days 0, 30 and 90. Five animals were used per group.

As can be seen in Table 7, the internal CHO E2 preparation produced blocking antibodies that appeared to be as high or higher than those antibodies produced by HeLa E1/E2-immunized guinea pigs. The secreted CHO E2 preparations did not produce detectable blocking antibodies. These results suggest that intracellularly produced E2 is far superior to the secreted extracellular form in inducing neutralizing antibodies.

TABLE 7

Blocking antibodies to the putative receptor in immunized guinea pigs.

| E2 Prep | Group # | Dose | NOB (E2-1a) | NOB (E2-1b) |
|---|---|---|---|---|
| Internal CHO E2 | 5 | 80 μg | 700 | 80 |
| | 6 | 8.0 μg | 1000 | ND |
| | 7 | 0.8 μg | 1500 | ND |
| | 8 | 8, 2, 0.8 μg | 1000 | 100 |
| Secreted CHO E2 | 9 | 80 μg | 0 | ND |
| | 10 | 8.0 μg | 0 | ND |
| | 11 | 0.8 μg | 0 | ND |
| | 12 | 8, 2, 0.8 μg | 0 | ND |
| HeLa E1/E2 | 16 | 8, 2, 0.8 μg | 600 | 400 |

Also as shown in Table 7, the internal E2 antigen induced NOB titers to the HCV1a antigen in contrast to the lack of neutralizing antibodies induced by the secreted E2 antigen. Furthermore, guinea pigs immunized with the internal E2 antigen also developed antibodies that could cross-neutralize HCv1b E2 binding to the T-cell line used.

Thus, methods for obtaining intracellularly expressed E1 and E2 polypeptides are disclosed, as are methods of using the same. Although preferred embodiments of the subject invention have been described in some detail, it is understood that obvious variations can be made without departing from the spirit and the scope of the invention as defined by the appended claims.

We claim:

1. A method for isolating a hepatitis C virus (HCV) E2 polypeptide that lacks a portion of its C-terminus from about amino acid 715 to its C-terminus, numbered with reference to the HCV1 E2 amino acid sequence, said method comprising:

(a) providing a population of host mammalian, yeast, plant or bacterial cells transformed with a polynucleotide comprising a coding sequence for said HCV E2 polypeptide, wherein said coding sequence is operably linked to control elements such that said coding sequence can be transcribed and translated in the host cell;

(b) culturing said population of host cells under conditions whereby said HCV E2 polypeptide is expressed intracellularly;

(c) disrupting said host cells; and (d) isolating said HCV E2 polypeptide from said disrupted host cells.

2. The method of claim 1, wherein said HCV E2 polypeptide lacks at least a portion of its C-terminus beginning at about amino acid 625, numbered with reference to the HCV1 E2 amino acid sequence.

3. The method of claim 2, wherein said HCV E2 polypeptide is truncated after about amino acid 661, numbered with reference to the HCV1 E2 amino acid sequence.

4. The method of claim 2, wherein said HCV E2 polypeptide is truncated after about amino acid 655, numbered with reference to the HCV1 E2 amino acid sequence.

5. The method of claim 1, wherein said HCV E2 polypeptide is truncated after about amino acid 500, numbered with reference to the HCV1 E2 amino acid sequence.

6. The method of claim 1, wherein said isolating is done using affinity chromatography.

7. The method of claim 2, wherein said isolating is done using affinity chromatography.

8. The method of claim 3, wherein said isolating is done using affinity chromatography.

9. The method of claim 4, wherein said isolating is done using affinity chromatography.

10. The method of claim 6, wherein said affinity chromatography is GNA agarose chromatography.

11. The method of claim 7, wherein said affinity chromatography is GNA agarose chromatography.

12. The method of claim 8, wherein said affinity chromatography is GNA agarose chromatography.

13. The method of claim 9, wherein said affinity chromatography is GNA agarose chromatography.

* * * * *

SEQUENCE LISTING

<160> NUMBER OF SEQ ID NOS: 4

<210> SEQ ID NO 1
<211> LENGTH: 636
<212> TYPE: DNA
<213> ORGANISM: Hepatitis C virus
<220> FEATURE:
<221> NAME/KEY: CDS
<222> LOCATION: (1)..(633)

<400> SEQUENCE: 1

```
atg att tgc tct ttc tct atc ttc ctt ctg gcc ctg ctc tct tgc ttg      48
Met Ile Cys Ser Phe Ser Ile Phe Leu Leu Ala Leu Leu Ser Cys Leu
 1               5                  10                  15
```

```
act gtg ccc gct tcg gcc tac caa gtg cgc aac tcc acg ggg ctc tac       96
Thr Val Pro Ala Ser Ala Tyr Gln Val Arg Asn Ser Thr Gly Leu Tyr
         20                  25                  30 cac gtc acc aat gat tgc cct aac tcg agt att gtg tac gag gcg gcc      144
His Val Thr Asn Asp Cys Pro Asn Ser Ser Ile Val Tyr Glu Ala Ala
             35                  40                  45 gat gcc atc ctg cac act ccg ggg tgc gtc cct tgc gtt cgt gag ggc      192
Asp Ala Ile Leu His Thr Pro Gly Cys Val Pro Cys Val Arg Glu Gly
 50                  55                  60 aac gcc tcg agg tgt tgg gtg gcg atg acc cct acg gtg gcc acc agg      240
Asn Ala Ser Arg Cys Trp Val Ala Met Thr Pro Thr Val Ala Thr Arg
 65                  70                  75                  80 gat ggc aaa ctc ccc gcg acg cag ctt cga cgt cac atc gat ctg ctt      288
Asp Gly Lys Leu Pro Ala Thr Gln Leu Arg Arg His Ile Asp Leu Leu
                 85                  90                  95 gtc ggg agc gcc acc ctc tgt tcg gcc ctc tac gtg ggg gac ctc tgc      336
Val Gly Ser Ala Thr Leu Cys Ser Ala Leu Tyr Val Gly Asp Leu Cys
            100                 105                 110 ggg tct gtc ttt ctt gtc ggc caa ctg ttt acc ttc tct ccc agg cgc      384
Gly Ser Val Phe Leu Val Gly Gln Leu Phe Thr Phe Ser Pro Arg Arg
        115                 120                 125 cac tgg acg acg caa ggt tgc aat tgc tct atc tat ccc ggc cat ata      432
His Trp Thr Thr Gln Gly Cys Asn Cys Ser Ile Tyr Pro Gly His Ile
130                 135                 140 acg ggt cac cgc atg gca tgg gat atg atg atg aac tgg tcc cct acg      480
Thr Gly His Arg Met Ala Trp Asp Met Met Met Asn Trp Ser Pro Thr
145                 150                 155                 160 acg gcg ttg gta atg gct cag ctg ctc cgg atc cca caa gcc atc ttg      528
Thr Ala Leu Val Met Ala Gln Leu Leu Arg Ile Pro Gln Ala Ile Leu
                165                 170                 175 gac atg atc gct ggt gct cac tgg gga gtc ctg gcg ggc ata gcg tat      576
Asp Met Ile Ala Gly Ala His Trp Gly Val Leu Ala Gly Ile Ala Tyr
            180                 185                 190 ttc tcc atg gtg ggg aac tgg gcg aag gtc ctg gta gtg ctg ctg cta      624
Phe Ser Met Val Gly Asn Trp Ala Lys Val Leu Val Val Leu Leu Leu
        195                 200                 205 ttt gcc ggc tga                                                      636
Phe Ala Gly
    210
```

<210> SEQ ID NO 2
<211> LENGTH: 211
<212> TYPE: PRT
<213> ORGANISM: Hepatitis C virus

<400> SEQUENCE: 2

```
Met Ile Cys Ser Phe Ser Ile Phe Leu Leu Ala Leu Leu Ser Cys Leu
 1               5                  10                  15

Thr Val Pro Ala Ser Ala Tyr Gln Val Arg Asn Ser Thr Gly Leu Tyr
         20                  25                  30

His Val Thr Asn Asp Cys Pro Asn Ser Ser Ile Val Tyr Glu Ala Ala
             35                  40                  45

Asp Ala Ile Leu His Thr Pro Gly Cys Val Pro Cys Val Arg Glu Gly
 50                  55                  60

Asn Ala Ser Arg Cys Trp Val Ala Met Thr Pro Thr Val Ala Thr Arg
 65                  70                  75                  80

Asp Gly Lys Leu Pro Ala Thr Gln Leu Arg Arg His Ile Asp Leu Leu
                 85                  90                  95
```

```
Val Gly Ser Ala Thr Leu Cys Ser Ala Leu Tyr Val Gly Asp Leu Cys
            100                 105                 110

Gly Ser Val Phe Leu Val Gly Gln Leu Phe Thr Phe Ser Pro Arg Arg
        115                 120                 125

His Trp Thr Thr Gln Gly Cys Asn Cys Ser Ile Tyr Pro Gly His Ile
    130                 135                 140

Thr Gly His Arg Met Ala Trp Asp Met Met Asn Trp Ser Pro Thr
145                 150                 155                 160

Thr Ala Leu Val Met Ala Gln Leu Leu Arg Ile Pro Gln Ala Ile Leu
                165                 170                 175

Asp Met Ile Ala Gly Ala His Trp Gly Val Leu Ala Gly Ile Ala Tyr
                180                 185                 190

Phe Ser Met Val Gly Asn Trp Ala Lys Val Leu Val Val Leu Leu Leu
            195                 200                 205

Phe Ala Gly
    210

<210> SEQ ID NO 3
<211> LENGTH: 1989
<212> TYPE: DNA
<213> ORGANISM: Hepatitis C virus
<220> FEATURE:
<221> NAME/KEY: CDS
<222> LOCATION: (1)..(1989)

<400> SEQUENCE: 3 atg gtg ggg aac tgg gcg aag gtc ctg gta gtg ctg ctg cta ttt gcc        48
Met Val Gly Asn Trp Ala Lys Val Leu Val Val Leu Leu Leu Phe Ala
  1               5                  10                  15 ggc gtc gac gcg gaa acc cac gtc acc ggg gga agt gcc ggc cac act        96
Gly Val Asp Ala Glu Thr His Val Thr Gly Gly Ser Ala Gly His Thr
                 20                  25                  30 gtg tct gga ttt gtt agc ctc ctc gca cca ggc gcc aag cag aac gtc       144
Val Ser Gly Phe Val Ser Leu Leu Ala Pro Gly Ala Lys Gln Asn Val
             35                  40                  45 cag ctg atc aac acc aac ggc agt tgg cac ctc aat agc acg gcc ctg       192
Gln Leu Ile Asn Thr Asn Gly Ser Trp His Leu Asn Ser Thr Ala Leu
         50                  55                  60 aac tgc aat gat agc ctc aac acc ggc tgg ttg gca ggg ctt ttc tat       240
Asn Cys Asn Asp Ser Leu Asn Thr Gly Trp Leu Ala Gly Leu Phe Tyr
 65                  70                  75                  80 cac cac aag ttc aac tct tca ggc tgt cct gag agg cta gcc agc tgc       288
His His Lys Phe Asn Ser Ser Gly Cys Pro Glu Arg Leu Ala Ser Cys
                     85                  90                  95 cga ccc ctt acc gat ttt gac cag ggc tgg ggc cct atc agt tat gcc       336
Arg Pro Leu Thr Asp Phe Asp Gln Gly Trp Gly Pro Ile Ser Tyr Ala
                100                 105                 110 aac gga agc ggc ccc gac cag cgc ccc tac tgc tgg cac tac ccc cca       384
Asn Gly Ser Gly Pro Asp Gln Arg Pro Tyr Cys Trp His Tyr Pro Pro
            115                 120                 125 aaa cct tgc ggt att gtg ccc gcg aag agt gtg tgt ggt ccg gta tat       432
Lys Pro Cys Gly Ile Val Pro Ala Lys Ser Val Cys Gly Pro Val Tyr
        130                 135                 140 tgc ttc act ccc agc ccc gtg gtg gtg gga acg acc gac agg tcg ggc       480
Cys Phe Thr Pro Ser Pro Val Val Val Gly Thr Thr Asp Arg Ser Gly
145                 150                 155                 160 gcg ccc acc tac agc tgg ggt gaa aat gat acg gac gtc ttc gtc ctt       528
Ala Pro Thr Tyr Ser Trp Gly Glu Asn Asp Thr Asp Val Phe Val Leu
                165                 170                 175
```

```
aac aat acc agg cca ccg ctg ggc aat tgg ttc ggt tgt acc tgg atg         576
Asn Asn Thr Arg Pro Pro Leu Gly Asn Trp Phe Gly Cys Thr Trp Met
        180                 185                 190 aac tca act gga ttc acc aaa gtg tgc gga gcg cct cct tgt gtc atc         624
Asn Ser Thr Gly Phe Thr Lys Val Cys Gly Ala Pro Pro Cys Val Ile
    195                 200                 205 gga ggg gcg ggc aac aac acc ctg cac tgc ccc act gat tgc ttc cgc         672
Gly Gly Ala Gly Asn Asn Thr Leu His Cys Pro Thr Asp Cys Phe Arg
210                 215                 220 aag cat ccg gac gcc aca tac tct cgg tgc ggc tcc ggt ccc tgg atc         720
Lys His Pro Asp Ala Thr Tyr Ser Arg Cys Gly Ser Gly Pro Trp Ile
225                 230                 235                 240 aca ccc agg tgc ctg gtc gac tac ccg tat agg ctt tgg cat tat cct         768
Thr Pro Arg Cys Leu Val Asp Tyr Pro Tyr Arg Leu Trp His Tyr Pro
                245                 250                 255 tgt acc atc aac tac acc ata ttt aaa atc agg atg tac gtg gga ggg         816
Cys Thr Ile Asn Tyr Thr Ile Phe Lys Ile Arg Met Tyr Val Gly Gly
            260                 265                 270 gtc gaa cac agg ctg gaa gct gcc tgc aac tgg acg cgg ggc gaa cgt         864
Val Glu His Arg Leu Glu Ala Ala Cys Asn Trp Thr Arg Gly Glu Arg
        275                 280                 285 tgc gat ctg gaa gat agg gac agg tcc gag ctc agc ccg tta ctg ctg         912
Cys Asp Leu Glu Asp Arg Asp Arg Ser Glu Leu Ser Pro Leu Leu Leu
290                 295                 300 acc act aca cag tgg cag gtc ctc ccg tgt tcc ttc aca acc ctg cca         960
Thr Thr Thr Gln Trp Gln Val Leu Pro Cys Ser Phe Thr Thr Leu Pro
305                 310                 315                 320 gcc ttg tcc acc ggc ctc atc cac ctc cac cag aac att gtg gac gtg        1008
Ala Leu Ser Thr Gly Leu Ile His Leu His Gln Asn Ile Val Asp Val
                325                 330                 335 cag tac ttg tac ggg gtg ggg tca agc atc gcg tcc tgg gcc att aag        1056
Gln Tyr Leu Tyr Gly Val Gly Ser Ser Ile Ala Ser Trp Ala Ile Lys
            340                 345                 350 tgg gag tac gtc gtc ctc ctg ttc ctt ctg ctt gca gac gcg cgc gtc        1104
Trp Glu Tyr Val Val Leu Leu Phe Leu Leu Leu Ala Asp Ala Arg Val
        355                 360                 365 tgc tcc tgc ttg tgg atg atg cta ctc ata tcc caa gcg gaa gcg gct        1152
Cys Ser Cys Leu Trp Met Met Leu Leu Ile Ser Gln Ala Glu Ala Ala
370                 375                 380 ttg gag aac ctc gta ata ctt aat gca gca tcc ctg gcc ggg acg cac        1200
Leu Glu Asn Leu Val Ile Leu Asn Ala Ala Ser Leu Ala Gly Thr His
385                 390                 395                 400 ggt ctt gta tcc ttc ctc gtg ttc ttc tgc ttt gca tgg tat ctg aag        1248
Gly Leu Val Ser Phe Leu Val Phe Phe Cys Phe Ala Trp Tyr Leu Lys
                405                 410                 415 ggt aag tgg gtg ccc gga gcg gtc tac acc ttc tac ggg atg tgg cct        1296
Gly Lys Trp Val Pro Gly Ala Val Tyr Thr Phe Tyr Gly Met Trp Pro
            420                 425                 430 ctc ctc ctg ctc ctg ttg gcg ttg ccc cag cgg gcg tac gcg ctg gac        1344
Leu Leu Leu Leu Leu Leu Ala Leu Pro Gln Arg Ala Tyr Ala Leu Asp
        435                 440                 445 acg gag gtg gcc gcg tcg tgt ggc ggt gtt gtt ctc gtc ggg ttg atg        1392
Thr Glu Val Ala Ala Ser Cys Gly Gly Val Val Leu Val Gly Leu Met
450                 455                 460 gcg cta act ctg tca cca tat tac aag cgc tat atc agc tgg tgc tta        1440
Ala Leu Thr Leu Ser Pro Tyr Tyr Lys Arg Tyr Ile Ser Trp Cys Leu
465                 470                 475                 480 tgg tgg ctt cag tat ttt ctg acc agg gtg gaa gcg caa ctg cac gtg        1488
Trp Trp Leu Gln Tyr Phe Leu Thr Arg Val Glu Ala Gln Leu His Val
                485                 490                 495
```

-continued

```
tgg att ccc ccc ctc aac gtc cga ggg ggg cgc gac gcc gtc atc tta     1536
Trp Ile Pro Pro Leu Asn Val Arg Gly Gly Arg Asp Ala Val Ile Leu
        500                 505                 510 ctc atg tgt gct gta cac ccg act ctg gta ttt gac atc acc aaa ttg     1584
Leu Met Cys Ala Val His Pro Thr Leu Val Phe Asp Ile Thr Lys Leu
    515                 520                 525 ctg ctg gcc gtc ttc gga ccc ctt tgg att ctt caa gcc agt ttg ctt     1632
Leu Leu Ala Val Phe Gly Pro Leu Trp Ile Leu Gln Ala Ser Leu Leu
530                 535                 540 aaa gta ccc tac ttt gtg cgc gtc caa ggc ctt ctc cgg ttc tgc gcg     1680
Lys Val Pro Tyr Phe Val Arg Val Gln Gly Leu Leu Arg Phe Cys Ala
545                 550                 555                 560 tta gcg cgg aag atg atc gga ggc cat tac gtg caa atg gtc atc att     1728
Leu Ala Arg Lys Met Ile Gly Gly His Tyr Val Gln Met Val Ile Ile
                565                 570                 575 aag tta ggg gcg ctt act ggc acc tat gtt tat aac cat ctc act cct     1776
Lys Leu Gly Ala Leu Thr Gly Thr Tyr Val Tyr Asn His Leu Thr Pro
            580                 585                 590 ctt cgg gac tgg gcg cac aac ggc ttg cga gat ctg gcc gtg gct gta     1824
Leu Arg Asp Trp Ala His Asn Gly Leu Arg Asp Leu Ala Val Ala Val
        595                 600                 605 gag cca gtc gtc ttc tcc caa atg gag acc aag ctc atc acg tgg ggg     1872
Glu Pro Val Val Phe Ser Gln Met Glu Thr Lys Leu Ile Thr Trp Gly
    610                 615                 620 gca gat acc gcc gcg tgc ggt gac atc atc aac ggc ttg cct gtt tcc     1920
Ala Asp Thr Ala Ala Cys Gly Asp Ile Ile Asn Gly Leu Pro Val Ser
625                 630                 635                 640 gcc cgc agg ggc cgg gag ata ctg ctc ggg cca gcc gat gga atg gtc     1968
Ala Arg Arg Gly Arg Glu Ile Leu Leu Gly Pro Ala Asp Gly Met Val
                645                 650                 655 tcc aag ggt tgg agg ttg ctg                                         1989
Ser Lys Gly Trp Arg Leu Leu
            660
```

<210> SEQ ID NO 4
<211> LENGTH: 663
<212> TYPE: PRT
<213> ORGANISM: Hepatitis C virus

<400> SEQUENCE: 4

```
Met Val Gly Asn Trp Ala Lys Val Leu Val Val Leu Leu Leu Phe Ala
 1               5                  10                  15

Gly Val Asp Ala Glu Thr His Val Thr Gly Gly Ser Ala Gly His Thr
                20                  25                  30

Val Ser Gly Phe Val Ser Leu Leu Ala Pro Gly Ala Lys Gln Asn Val
            35                  40                  45

Gln Leu Ile Asn Thr Asn Gly Ser Trp His Leu Asn Ser Thr Ala Leu
        50                  55                  60

Asn Cys Asn Asp Ser Leu Asn Thr Gly Trp Leu Ala Gly Leu Phe Tyr
65                  70                  75                  80

His His Lys Phe Asn Ser Ser Gly Cys Pro Glu Arg Leu Ala Ser Cys
                85                  90                  95

Arg Pro Leu Thr Asp Phe Asp Gln Gly Trp Gly Pro Ile Ser Tyr Ala
            100                 105                 110

Asn Gly Ser Gly Pro Asp Gln Arg Pro Tyr Cys Trp His Tyr Pro Pro
        115                 120                 125

Lys Pro Cys Gly Ile Val Pro Ala Lys Ser Val Cys Gly Pro Val Tyr
130                 135                 140
```

```
Cys Phe Thr Pro Ser Pro Val Val Gly Thr Asp Arg Ser Gly
145                 150                 155                 160

Ala Pro Thr Tyr Ser Trp Gly Glu Asn Asp Thr Asp Val Phe Val Leu
                165                 170                 175

Asn Asn Thr Arg Pro Pro Leu Gly Asn Trp Phe Gly Cys Thr Trp Met
            180                 185                 190

Asn Ser Thr Gly Phe Thr Lys Val Cys Gly Ala Pro Pro Cys Val Ile
        195                 200                 205

Gly Gly Ala Gly Asn Asn Thr Leu His Cys Pro Thr Asp Cys Phe Arg
210                 215                 220

Lys His Pro Asp Ala Thr Tyr Ser Arg Cys Gly Ser Gly Pro Trp Ile
225                 230                 235                 240

Thr Pro Arg Cys Leu Val Asp Tyr Pro Tyr Arg Leu Trp His Tyr Pro
                245                 250                 255

Cys Thr Ile Asn Tyr Thr Ile Phe Lys Ile Arg Met Tyr Val Gly Gly
            260                 265                 270

Val Glu His Arg Leu Glu Ala Ala Cys Asn Trp Thr Arg Gly Glu Arg
        275                 280                 285

Cys Asp Leu Glu Asp Arg Asp Arg Ser Glu Leu Ser Pro Leu Leu Leu
290                 295                 300

Thr Thr Thr Gln Trp Gln Val Leu Pro Cys Ser Phe Thr Thr Leu Pro
305                 310                 315                 320

Ala Leu Ser Thr Gly Leu Ile His Leu His Gln Asn Ile Val Asp Val
                325                 330                 335

Gln Tyr Leu Tyr Gly Val Gly Ser Ser Ile Ala Ser Trp Ala Ile Lys
            340                 345                 350

Trp Glu Tyr Val Val Leu Leu Phe Leu Leu Leu Ala Asp Ala Arg Val
        355                 360                 365

Cys Ser Cys Leu Trp Met Met Leu Leu Ile Ser Gln Ala Glu Ala Ala
370                 375                 380

Leu Glu Asn Leu Val Ile Leu Asn Ala Ala Ser Leu Ala Gly Thr His
385                 390                 395                 400

Gly Leu Val Ser Phe Leu Val Phe Phe Cys Phe Ala Trp Tyr Leu Lys
                405                 410                 415

Gly Lys Trp Val Pro Gly Ala Val Tyr Thr Phe Tyr Gly Met Trp Pro
            420                 425                 430

Leu Leu Leu Leu Leu Leu Ala Leu Pro Gln Arg Ala Tyr Ala Leu Asp
        435                 440                 445

Thr Glu Val Ala Ala Ser Cys Gly Gly Val Val Leu Val Gly Leu Met
450                 455                 460

Ala Leu Thr Leu Ser Pro Tyr Tyr Lys Arg Tyr Ile Ser Trp Cys Leu
465                 470                 475                 480

Trp Trp Leu Gln Tyr Phe Leu Thr Arg Val Glu Ala Gln Leu His Val
                485                 490                 495

Trp Ile Pro Pro Leu Asn Val Arg Gly Gly Arg Asp Ala Val Ile Leu
            500                 505                 510

Leu Met Cys Ala Val His Pro Thr Leu Val Phe Asp Ile Thr Lys Leu
        515                 520                 525

Leu Leu Ala Val Phe Gly Pro Leu Trp Ile Leu Gln Ala Ser Leu Leu
530                 535                 540

Lys Val Pro Tyr Phe Val Arg Val Gln Gly Leu Leu Arg Phe Cys Ala
545                 550                 555                 560
```

-continued

```
Leu Ala Arg Lys Met Ile Gly Gly His Tyr Val Gln Met Val Ile Ile
                565                 570                 575

Lys Leu Gly Ala Leu Thr Gly Thr Tyr Val Tyr Asn His Leu Thr Pro
            580                 585                 590

Leu Arg Asp Trp Ala His Asn Gly Leu Arg Asp Leu Ala Val Ala Val
        595                 600                 605

Glu Pro Val Val Phe Ser Gln Met Glu Thr Lys Leu Ile Thr Trp Gly
    610                 615                 620

Ala Asp Thr Ala Ala Cys Gly Asp Ile Ile Asn Gly Leu Pro Val Ser
625                 630                 635                 640

Ala Arg Arg Gly Arg Glu Ile Leu Leu Gly Pro Ala Asp Gly Met Val
                645                 650                 655

Ser Lys Gly Trp Arg Leu Leu
            660
```